(12) United States Patent
Sohda et al.

(10) Patent No.: US 6,214,838 B1
(45) Date of Patent: Apr. 10, 2001

(54) THIENODIPYRIDINE DERIVATIVES, PRODUCTION AND USE THEREOF

(75) Inventors: Takashi Sohda, Takatsuki; Haruhiko Makino, Hyogo; Atsuo Baba, Ashiya; Taihei Yamane, Ikeda, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/355,218

(22) PCT Filed: Jun. 14, 1999

(86) PCT No.: PCT/JP99/03155

§ 371 Date: Jul. 23, 1999

§ 102(e) Date: Jul. 23, 1999

(87) PCT Pub. No.: WO99/65916

PCT Pub. Date: Dec. 23, 1999

(30) Foreign Application Priority Data

Jun. 15, 1998 (JP) .................................................. 10-166910

(51) Int. Cl.$^7$ ................ A61K 31/4365; A61K 31/4375; C07D 495/14; A61P 29/00
(52) U.S. Cl. ............................................. 514/293; 546/83
(58) Field of Search ................................ 514/293; 546/83

(56) References Cited

U.S. PATENT DOCUMENTS 6,046,189 * 4/2000 Sohda .................................. 514/212

FOREIGN PATENT DOCUMENTS

WO 97/40050 10/1997 (WO) .

* cited by examiner

*Primary Examiner*—Evelyn Mei Huang
(74) *Attorney, Agent, or Firm*—Philippe Y. Riesen; Mark Chao

(57) ABSTRACT

A compound of the formula (I):

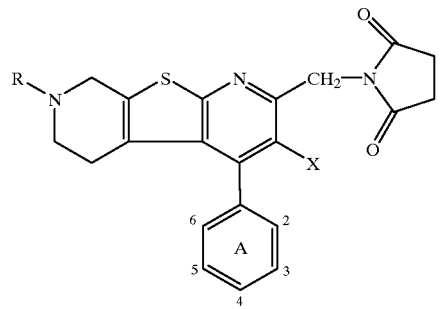

wherein R is hydrogen or $C_{2-6}$ alkanoyl; X is halogen; and ring A is benzene ring which is optionally substituted by 1 to 4 substituents selected from ① halogen, ② hydroxy, ③ $C_{1-6}$ alkoxy optionally substituted by halogen or phenyl, ④ $C_{1-6}$ alkylthio optionally substituted by halogen or phenyl, ⑤ $C_{1-6}$ alkyl optionally substituted by halogen, ⑥ $C_{2-6}$ alkanoylamino or ⑦ carboxy optionally esterified by $C_{1-6}$ alkyl, or a salt thereof; which can be used for preventing or treating inflammatory disease, arthritis, chronic rheumatoid arthritis, autoimmune diseases, or rejection after organ transplantation.

33 Claims, No Drawings

THIENODIPYRIDINE DERIVATIVES, PRODUCTION AND USE THEREOF

This application is the National Stage of International Application No. PCT/JP99/03155, filed on Jun. 14, 1999.

TECHNICAL FIELD

The present invention relates to a new thienodipyridine derivative which shows anti-inflammatory activity, bone resorption inhibitory activity and activity on inhibiting production of immunocytokines and which is useful as a therapeutic agent for arthritis, or a salt thereof, production thereof and use thereof.

BACKGROUND ART

Arthritis, an inflammatory disease of the joint, occurs in various forms such as rheumatoid arthritis and in related diseases with joint inflammation.

Rheumatoid arthritis, also called chronic rheumatoid arthritis, in particular, is a chronic multiple arthritis characterized by inflammatory changes in the synovial membrane of the particular capsule inner layer. Arthritis like rheumatoid arthritis are progressive and cause joint disorders such as deformation and acampsia, often resulting in severe physical disorders due to a lack of effective treatment and subsequent deterioration.

Traditionally, these forms of arthritis have been chemotherapeutically treated with various agents, including steroids and other adrenocortical hormones (e.g., cortisone), non-steroidal anti-inflammatory agents (e.g., aspirin, piroxicam, indomethacin), gold agents (e.g., aurothiomalate), antirheumaticagents (e.g., chloroquine preparations, D-penicillamine), anti-gout agents (e.g., colchicine), and immunosuppressors (e.g., cyclophosphamide, azathioprine, methotrexate, levamisole).

Japanese laid-open Publication No. 10-36374 (1998) or PCT International Application Laid-Open No. WO97/40050 show thienopyridine derivatives or thienodipyridine, derivatives as an anti-inflammatory agent, especially as a therapeutic agent for arthritis.

However, steroids such as adrenocortical hormones and non-steroidal anti-inflammatory agents have drawbacks such as severe adverse reactions and adverse reactions hampering the drug's long-term use.

Although thienopyridine derivatives and thienodipyridine derivatives concretely disclosed in Japanese laid-open Publication No. 10-36374 (1998) or PCT International Application Laid-Open No. WO97/40050 have an anti-inflammatory activity, and especially therapeutic effect for arthritis, they tend to be affected by the metabolism of the body, so that, ratio of non-metabolized form of these derivatives in a body also tends to be lower.

Accordingly, there is a need for the development of a drug which is stable to metabolism by the body and exhibits excellent anti-inflammatory activity, bone resorption inhibitory activity and activity in inhibiting production of immunocytokines.

DISCLOSURE OF INVENTION

The present inventors studied in accordance with the above states, and found that thienodipyridine derivatives having succinimidomethyl group at the 2-position and non-substituted or alkanoyl group as a protective group at the 7-position show strong anti-inflammatory activity, especially anti-arthritic activity, and that these derivatives are stable to metabolism by the body. The inventors made investigations based on these findings, and developed the present invention.

The present invention relates to (1) a compound of the formula (I):

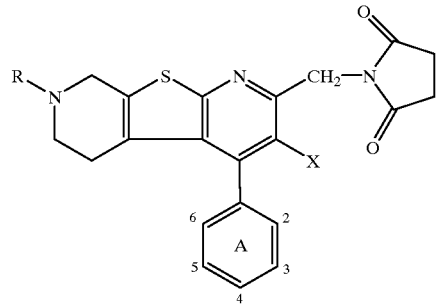

wherein R is hydrogen or $C_{2-6}$ alkanoyl; X is halogen; and ring A is benzene ring which is optionally substituted by 1 to 4 substituents selected from ① halogen, ② hydroxy, ③ $C_{1-6}$ alkoxy optionally substituted by halogen or phenyl, ④ $C_{1-6}$ alkylthio optionally substituted by halogen or phenyl, ⑤ $C_{1-6}$ alkyl optionally substituted by halogen, ⑥ $C_{2-6}$ alkanoylamino or ⑦ carboxy optionally esterified by $C_{1-6}$ alkyl, or a salt thereof;

(2) a compound of the above (1) wherein R is hydrogen;

(3) a compound of the above (1) wherein ring A is benzene ring which is optionally substituted by 1 to 2 substituents selected from ① hydroxy, ② $C_{1-6}$ alkoxy optionally substituted by halogen or ③ $C_{1-6}$ alkylthio optionally substituted by halogen;

(4) a compound of the above (1) wherein R is hydrogen; and ring A is benzene ring which is optionally substituted by 1 to 2 substituents selected from ① $C_{1-6}$ alkoxy optionally substituted by halogen or ② $C_{1-6}$ alkylthio optionally substituted by halogen;

(5) a compound of the above (1) wherein R is hydrogen; X is chlorine; and ring A is benzene ring which is optionally substituted by 1 to 2 $C_{1-6}$ alkoxy groups, or a salt thereof;

(6) a compound of the above (5) wherein ring A is benzene ring substituted by $C_{1-6}$ alkoxy group at the 4-position and optionally substituted by $C_{1-6}$ alkoxy group at the other position;

(7) a compound of the above (1) wherein R is hydrogen; X is chlorine; and ring A is benzene ring which is optionally substituted by 1 to 2 methoxy groups;

(8) a compound of the above (1) wherein R is $C_{2-6}$ alkanoyl; and ring A is benzene ring which is optionally substituted by 1 to 2 substituents selected from ① hydroxy, ② $C_{1-6}$ alkoxy optionally substituted by halogen or ③ $C_{1-6}$ alkylthio optionally substituted by halogen;

(9) a pro-drug of the compound of the above (1);

(10) 3-chloro-5,6,7,8-tetrahydro-4-(4-methoxyphenyl)-2-(succinimidomethyl)thieno[2,3-b:5,4-c']dipyridine, 3-chloro-4-(3,4-dimethoxyphenyl)-5,6,7,8-tetrahydro-2-(succinimidomethyl)thieno[2,3-b:5,4-c']dipyridine, or a salt thereof;

(11) 3-chloro-4-(4-ethoxyphenyl)-5,6,7,8-tetrahydro-2-(succinimidomethyl)thieno[2,3-b:5,4-c']dipyridine, 3-bromo-5,6,7,8-tetrahydro-4-(4-methoxyphenyl)-2-(succinimidomethyl)thieno[2,3-b:5,4-c']dipyridine, or a salt thereof;

(12) 7-acetyl-3-chloro-5,6,7,8-tetrahydro-4-(4-hydroxy-3-methoxyphenyl)-2-(succinimidomethyl)thieno[2,3-b:5,4-c']dipyridine, 7-acetyl-3-chloro-5,6,7,8-tetrahydro-4-(4-hydroxyphenyl)-2-(succinimidomethyl)thieno[2,3-b:5,4-c']dipyridine, or a salt thereof;

(13) 7-acetyl-3-chloro-5,6,7,8-tetrahydro-4-(4-methoxyphenyl)-2-(succinimidomethyl)thieno[2,3-b:5,4-c']dipyridine, 7-acetyl-3-chloro-4-(4-ethoxyphenyl)-5,6,7,8-tetrahydro-2-(succinimidomethyl)thieno[2,3-b:5,4-c']dipyridine, 7-acetyl-3-chloro-4-(3,4-dimethoxyphenyl)-5,6,7,8-tetrahydro-2-(succinimidomethyl)thieno[2,3-b:5,4-c']dipyridine, or a salt thereof;

(14) a method for production of a compound of the formula (I-2):

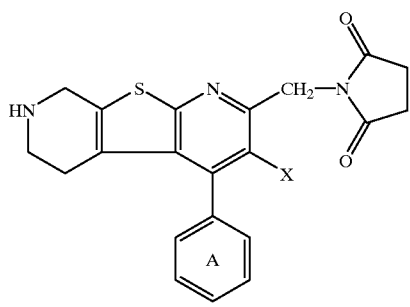

wherein X is halogen atom; and ring A is benzene ring which is optionally substituted by 1 to 4 substituents selected from ① halogen, ② hydroxy, ③ $C_{1-6}$ alkoxy optionally substituted by halogen or phenyl, ④ $C_{1-6}$ alkylthio optionally substituted by halogen or phenyl, ⑤ $C_{1-6}$ alkyl optionally substituted by halogen, By ⑥ $C_{2-6}$ alkanoylamino or ⑦ carboxyl optionally esterified by $C_{1-6}$ alkyl, or a salt thereof, which comprises subjecting a compound of the formula:

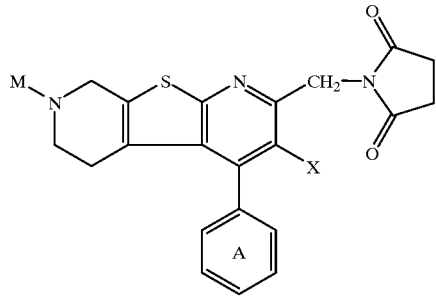

wherein M is a protective group of a nitrogen atom; the other symbols are the same defined above, or a salt thereof, to deprotection;

(15) a method for production of a compound of the formula (I-3):

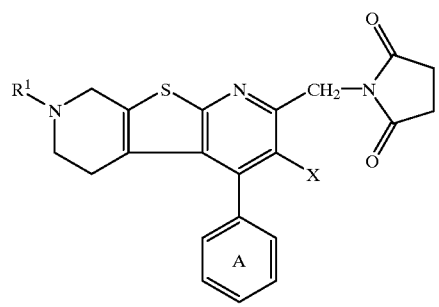

wherein $R^1$ is $C_{2-6}$ alkanoyl; X is halogen; ring A is benzene ring which is optionally substituted by 1 to 4 substituents selected from ① halogen, ② hydroxy, ③ $C_{1-6}$ alkoxy optionally substituted by halogen or phenyl, ④ $C_{1-6}$ alkylthio optionally substituted by halogen or phenyl ⑤ $C_{1-6}$ alkyl optionally substituted by halogen ⑥ $C_{2-6}$ alkanoylamino or ⑦ carboxyl optionally esterified by $C_{1-6}$ alkyl, or a salt thereof, which comprises subjecting a compound of the formula (I-2):

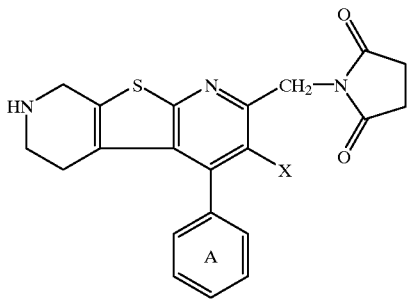

wherein each a symbol is the same defined above, or a salt thereof, to acylation;

(16) a pharmaceutical composition comprising a compound of the formula (I):

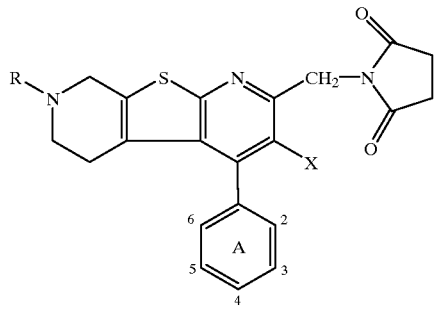

wherein R is hydrogen or $C_{2-6}$ alkanoyl; X is halogen; and ring A is benzene ring which is optionally substituted by 1 to 4 substituents selected from ① halogen, ② hydroxy, ③ $C_{1-6}$ alkoxy optionally substituted by halogen or phenyl, ④ $C_{1-6}$ alkylthio optionally substituted by halogen or phenyl, ⑤ $C_{1-6}$ alkyl optionally substituted by halogen ⑥ $C_{2-6}$ alkanoylamino or ⑦ carboxyl optionally esterified by $C_{1-6}$ alkyl, or a salt thereof;

(17) a pharmaceutical composition of the above (16) which is for preventing or treating inflammatory disease;

(18) a pharmaceutical composition of the above (16) which is for preventing or treating arthritis;

(19) a pharmaceutical composition of the above (16) which is for preventing or treating rheumatism;

(20) a pharmaceutical composition of the above (16) which is for preventing or treating chronic rheumatoid arthritis;

(21) a pharmaceutical composition of the above (16) which is for preventing or treating autoimmune disease;

(22) a pharmaceutical composition of the above (16) which is for preventing or treating rejection after organ transplantation;

(23) a method for preventing or treating inflammatory disease in a mammal which comprises administering an effective amount of the pharmaceutical composition of the above (16) to said mammal in need thereof;

(24) a method for preventing or treating arthritis in a mammal which comprises administering an effective amount of the pharmaceutical composition of the above (16) to said mammal in need thereof;

(25) a method for preventing or treating rheumatism in a mammal which comprises administering an effective amount: of the pharmaceutical composition of the above (16) to said mammal in need thereof;

(26) a method for preventing or treating chronic rheumatoid arthritis in a mammal which comprises administering an effective amount of the pharmaceutical composition of the above (16) to said mammal in need thereof;

(27) a method for preventing or treating autoimmune disease in a mammal which comprises administering an effective amount of the pharmaceutical composition of the above (16) to said mammal in need thereof;

(28) a method for preventing or treating rejection after organ transplantation in a mammal which comprises administering an effective amount of the pharmaceutical composition of the above (16) to said mammal in need thereof;

(29) use of the compound of the above (1) for manufactures of a pharmaceutical composition for preventing or treating inflammatory disease;

(30) use of the compound of the above (1) for manufacture of a pharmaceutical composition for preventing or treating arthritis;

(31) use of the compound of the above (1) for manufacture of a pharmaceutical composition for preventing or treating chronic rheumatoid arthritis;

(32) use of the compound of the above (1) for manufacture of a pharmaceutical composition for preventing or treating autoimmune diseases; and

(33) use of the compound of the above (1) for manufacture of a pharmaceutical composition for preventing or treating rejection after organ transplantation.

Examples of the $C_{2-6}$ alkanoyl for R or $R^1$ includes acetyl, propionyl, butyryl, isobutyryl, valeryl, isovaleryl, pivaloyl and the like.

Examples of the halogen for X or the substituent for the ring A (including a substituent for the substituent) include chlorine, bromine, iodine, fluorine and the like. Preferably chlorine and bromine, more preferably chlorine are exemplified.

Examples of the $C_{1-6}$ alkoxy in the optionally substituted $C_{1-6}$ alkoxy as a substituent for the ring A include methoxy, ethoxy, propoxy, isopropoxy, butoxy, isobutoxy, sec-butoxy, tert-butoxy, pentyloxy, isopentyloxy, neopentyloxy, hexyloxy and the like. The adjacent $C_{1-6}$ alkoxy can be bonded to each other to form a fused ring. When the $C_{1-6}$ alkoxy is formed into the fused ring, example of the substituents include methylenedioxy, ethylenedioxy and the like.

Examples of the $C_{1-6}$ alkoxy substituted by haloger include trifluoromethoxy, 2,2,2-trifluoroethoxy and the like.

Examples of the $C_{1-6}$ alkoxy substituted by phenyl include benzyloxy, phenethyloxy, 1-phenylpropoxy, 2-phenylpropoxy, 3-phenylpropoxy, benzhydryloxy, trityloxy and the like.

Examples of the alkylthio in the optionally substituted $C_{1-6}$ alkylthio as a substituent for the ring A include methylthio, ethylthio, propylthio, isopropylthio, butylthio, isobutylthio, sec-butylthio, tert-butylthio, pentylthio, isopentylthio, neopentylthio, hexylthio and the like.

Examples of the $C_{1-6}$ alkylthio substituted by halogen include trifluoromethylthio, 2,2,2-trifluoroethylthio and the like.

Examples of the $C_{1-6}$ alkylthio substituted by phenyl include benzylthio, phenethylthio, 1-phenylpropylthio, 2-phenylpropylthio, 3-phenylpropylythio, benzhydrylthio, tritylthio and the like.

Examples of the $C_{1-6}$ alkyl in the optionally substituted $C_{1-6}$ alkyl as a substituent for the ring A include methyl, ethyl, propyl, isopropyl, butyl, isobutyl, sec-butyl, tert-butyl, pentyl, isopentyl, neopentyl, hexyl and the like.

Examples of the $C_{2-6}$ alkanoyl in the $C_{2-6}$ alkanoylamino as a substituent for the ring A include propionyl, butyryl, isobutyryl, valeryl, isovaleryl, pivaloyl and the like.

Examples of the $C_{1-6}$ alkyl in the carboxyl optionally esterified with $C_{1-6}$ alkyl as a substituent for the ring A include the same ones mentioned above.

The ring A optionally has 1 to 4 substituents mentioned above, preferably 1 to 2 substituents.

The position of one of substituents for the ring A is preferably at the 3 -, 4-, or 5-position, more preferably one of the substituents is at the 4-position. When one substituent exists on the ring A, it is preferably at the 4-position. When two substituents exists on the ring A, they are preferably at the 4-position and the other position, more preferably at the 4-position and either 3- or 5-position.

Preferable Examples of the $C_{2-6}$ alkanoyl for R include $C_{2-4}$ alkanoyl (e.g., acetyl, propionyl, butyryl, isobutyryl). Among these, acetyl and propionyl are more preferable, and acetyl is further more preferable.

Preferable substituents for the ring A include (1) hydroxy, (2) $C_{1-6}$ alkoxy optionally substituted by halogen, (3) $C_{1-6}$ alkylthio optionally substituted by halogen and the like. More preferable ones are (1) hydroxy, (2) $C_{1-6}$ alkoxy and (3) $C_{1-6}$ alkylthio. Among these, hydroxy, methoxy and methylthio are further more preferable.

The preferable number of the substituents on the ring A is 1 to 2.

The most preferable subsistent on the ring A is 1 to 2 methoxy groups.

When R is $C_{1-6}$ alkanoyl, the substituent for the ring A is preferably $C_{1-6}$ alkoxy optionally substituted by two of the same or different substituents selected from (1) hydroxy or (2) halogen.

The salt of compound (I) of the present invention and the salt of the starting compound for producing compound (I) are preferably a pharmaceutically acceptable salt, exemplified by salts with inorganic bases, salts with organic bases, salts with inorganic acids, salts with organic acids and salts with basic or acidic amino acids.

Preferable salts with inorganic bases include alkali metal salts such as sodium salt and potassium salt; alkaline earth metal salts such as calcium salt and magnesium salt; and aluminum salt and ammonium salt. Preferable salts with organic bases include salts with trimethylamine, triethylamine, pyridine, picoline, ethanolamine, diethanolamine, triethanolamine, dicyclohexylamine and N,N'-dibenzylethylenediamine. Preferable salts with inorganic acids include salts with hydrochloric acid, hydrobromic acid, nitric acid, sulfuric acid and phosphoric acid. Preferable salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid. Preferable salts with basic amino acids include salts with arginine, lysine and ornithine. Preferable salts with acidic amino acids include salts with aspartic acid and glutamic acid.

Compound (I) or a salt thereof may be a pro-drug. The pro-drug of compound (I) or a salt thereof means a compound which is converted to the compound (I) or a salt thereof under physiological conditions or with a reaction due to an enzynme, a gastric acid etc. in the living body, that is, ① a compound which is converted to compound (I) or a salt thereof with oxidation, reduction, hydrolysis, etc. with an enzyme; ② a compound which is converted to compound (I) or a salt thereof with gastric acid, etc. Examples of the pro-drug of compound (I) or a salt thereof include compounds wherein hydroxy groups of compound (I) or a salt thereof are substituted with acyl, alkyl, phosphoric acid, boric acid, etc. (e.g. compounds wherein hydroxy groups of compound (I) or a salt thereof are substituted with acetyl, palmitoyl, propanoyl, pivaloyl, succinyl, fumaryl, alanyl, dimethylaminomethylcarbonyl, etc.); compounds wherein carboxyl groups of compound (I) or a salt thereof are modified with ester, amide, etc. (e.g. compounds wherein carboxyl groups of compound (I) or salt thereof are modified with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, etc.); etc. Said pro-drug can be produced by per se known methods from compound (I) or a salt thereof.

The pro-drug of compound (I) or a salt thereof may be a compound which is converted into compound (I) or a salt thereof under the physiological condition as described in "Pharmaceutical Research and Development" vol. 7 (Drug design), pages 163–198 published in 1990 by Hirokawa Publishing Co. (Tokyo, Japan).

Compound (I) or a salt thereof may be marked by an isotope such as $^3H$, $^{14}C$, $^{35}S$, $^{125}I$ and the like.

Preferred examples of compound (I) or a salt thereof of the present invention include 3-chloro-4-(3,4-dimethoxyphenyl)-5,6,7,8-tetrahydro-2-(succinimidomethyl)thieno[2,3-b:5,4-c']dipyridine;

3-chloro-5,6,7,8-tetrahydro-4-(4-methoxyphenyl)-2-(succinimidomethyl)thieno[2,3-b:5,4-c']dipyridine;

3-chloro-4-(4-ethoxyphenyl)-5,6,7,8-tetrahydro-2-(succinimidomethyl)thieno[2,3-b:5,4-c']dipyridine;

3-bromo-5,6,7,8-tetrahydro-4-(4-methoxyphenyl)-2-(succinimidomethyl)thieno[2,3-b:5,4-c']dipyridine;

7-acetyl-3-chloro-5,6,7,8-tetrahydro-4-(4-hydroxy-3-methoxyphenyl)-2-(succinimidomethyl)thieno[2,3-b:5,4-c']dipyridine;

7-acetyl-3-chloro-5,6,7,8-tetrahydro-4-(4-hydroxyphenyl)-2-(succinimidomethyl)thieno[2,3-b:5,4-c']dipyridine;

7-acetyl-3-chloro-5,6,7,8-tetrahydro-4-(4-methoxyphenyl)-2-(succinimidomethyl)thieno[2,3-b:5,4-c']dipyridine:

7-acetyl-3-chloro-4-(4-ethoxyphenyl)-5,6,7,8-tetrahydr-2-(succinimidomethyl)thieno[2,3-b:5,4-c']dipyridine;

7-acetyl-3-chloro-4-(3,4-dimethoxyphenyl)-5,6,7,8-tetrahydro-2-(succinimidomethyl)thieno[2,3-b:5,4-c']dipyridine; and a salt thereof.

Compound (I) of the present invention or a salt thereof can be prepared by the following method.

As shown in the reaction scheme (Scheme 1), compound (II) described above or a salt thereof is subjected to deprotection to produce compound (I-2).

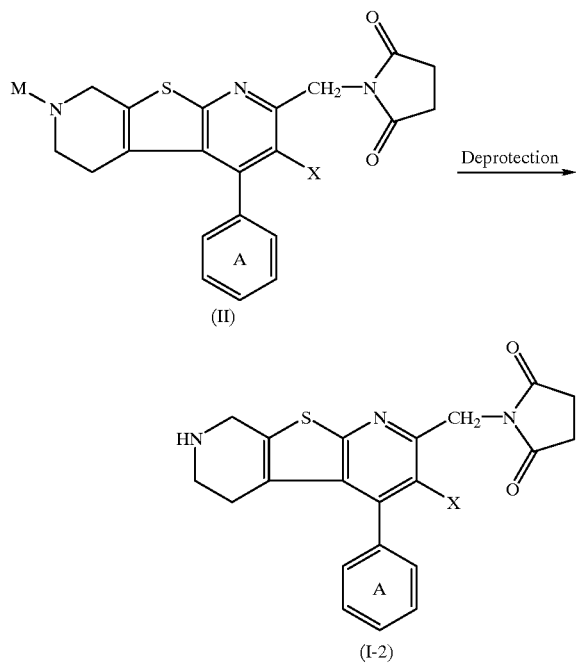

Scheme 1 wherein each symbol is the same as defined above.

A protective group represented by M in compound (II) includes, for example, an optionally substituted $C_{1-6}$ alkyl group, an optionally substituted $C_{1-6}$ alkanoyl group, an optionally substituted $C_{6-10}$ arylcarbonyl group, an optionally substituted $C_{6-10}$ arylsulfonyl group, an optionally substituted $C_{1-4}$ alkyloxycarbonyl group and the like. In these groups, 1 to 3 substituents may be present.

A $C_{1-6}$ alkyl group in said optionally substituted $C_{1-6}$ alkyl group may be those exemplified above. The substituent may for example be a $C_{6-10}$ aryl which may be substituted with a $C_{1-4}$ alkyl or a $C_{1-4}$ alkoxy. Examples of a substituted $C_{1-6}$ alkyl are benzyl, p-methoxybenzyl, trityl and the like.

A $C_{1-6}$ alkanoyl group in said optionally substituted $C_{1-6}$ alkanoyl group may for example be formyl, acetyl, propionyl, butyryl, valeryl, pivaloyl, succinyl, glutaryl and the like, and the substituent may for example be a halogen, oxo, a $C_{1-4}$ alkoxy and the like. An example of a substituted $C_{1-6}$ alkanoyl group is trifluoroacetyl.

A $C_{6-10}$ aryl in said optionally substituted $C_{6-10}$ arylcarbonyl group may for example be phenyl, naphthyl and the like. The substituent may for example be a halogen, nitro, hydroxy or oxo, a $C_{1-4}$ alkyl, a $C_{1-4}$ alkoxy and the like. An example of $C_{6-10}$ arylcarbonyl group is benzoyl.

A $C_{6-10}$ aryl in said optionally substituted $C_{6-10}$ arylsulfonyl group may be those exemplified above. The, substituent may for example be a halogen, nitro, hydroxy or oxo, a $C_{1-4}$ alkyl, a $C_{1-4}$ alkoxy and the like. An example of a $C_{6-10}$ arylsulfonyl is benzenesulfonyl. An example of a substituted $C_{6-10}$ arylsulfonyl is toluenesulfonyl.

A $C_{1-4}$ alkyl in said optionally substituted $C_{1-4}$ alkyloxycarbonyl group may be methyl, ethyl, n-propyl, n-butyl, t-butyl and the like. The substituent may for example be an optionally substituted $C_{6-10}$ aryl, a halogen, nitro, hydroxy or oxo, a $C_{1-4}$ alkyl, a $C_{1-4}$ alkoxy, a $C_{1-4}$ alkylthio and the like. Examples of an optionally substituted $C_{1-4}$ alkyloxycarbonyl group are ethoxycarbonyl, t-butyloxycarbonyl, benzyloxycarbonyl, p-methoxybenzyloxycarbonyl, p-nitrobenzyloxycarbonyl and the like.

In the above description, a $C_{6-10}$ aryl may for example be phenyl, naphthyl and the like. In the above description, a substituent in an optionally substituted $C_{6-10}$ aryl may, for example be nitro, a $C_{1-4}$ alkyl, a $C_{1-4}$ alkoxy and the like. In the above description, a $C_{1-4}$ alkyl may for example be methyl, ethyl, n-propyl, n-butyl, t-butyl and the like. In the above description, a $C_{1-4}$ alkoxy may for example be methoxy, ethoxy, propoxy, n-butoxy, t-butoxy and the like.

Said deprotection in the case where a protective group represented by M is an optionally substituted $C_{1-6}$ alkyl group and an optionally substituted $C_{1-4}$ alkyloxycarbonyl group can employ a catalytic hydrogenation (catalytic reduction)

A catalytic hydrogenation (catalytic reduction) may be effected by reacting a starting compound with hydrogen in the presence of a catalyst such as a palladium catalyst (e.g., palladium on carbon, palladium black, palladium hydroxide etc.) and a platinum catalyst (e.g., platinum oxide etc.).

When reacting with hydrogen, hydrogen or a hydrogen-generating compound is employed. The hydrogen-generating compound may for example be formic acid, ammonium formate, cyclohexanediene, cis-decalin, cyclohexene and the like.

Examples of a solvent employed in said catalytic hydrogenation (catalytic reduction) are alcohols (e.g., methanol, ethanol, n-propanol, isopropanol, n-butanol, 3-pentanol, etc.), aromatic hydrocarbons (e.g., benzene, toluene, xylene, etc.), saturated hydrocarbons (e.g., hexane, heptane, cyclohexane, etc.), ethers (e.g., diethylether, tetrahydrofuran, dioxane, dimethoxyethane, etc.), ketones (e.g., acetone, methylethylketone, etc.), nitriles (e.g., acetonitrile, etc.), sulfoxides (e.g., dimethylsulfoxide, etc.), amides (N,N-dimethylformamide, N,N-dimethylacetoamide, etc.), esters (e.g., ethyl acetate, etc.), carboxylic acids (e.g., acetic acid, propionic acid), pyridine, dimethoxyethane and the like.

The amount of a palladium catalyst or a platinum catalyst to be used is preferably about 200 mg to 4 g, more preferably about 500 mg to 2 g, per 1 g of a starting compound.

This reaction may be performed usually at a temperature of about 0 to 100° C., preferably about 10 to 40° C., and the reaction time is usually about 2 to 24 hours, preferably about 4 to 8 hours.

Said deprotection in the case where a protective group represented by M is an optionally substituted $C_{1-6}$ alkanoyl group or an optionally substituted $C_{6-10}$ arylcarbonyl group may preferably employ a hydrolysis under an acidic condition.

Examples of an acid to be employed are organic acids (e.g., formic acid, acetic acid, etc.) and inorganic acids (e.g., sulfuric acid, hydrochloric acid, phosphoric acid, hydrobromic acid, etc.).

Examples of a solvent employed in said hydrolysis are alcohols (e.g., methanol, ethanol, n-propanol, isopropanol, n-butanol, 3-pentanol, etc.), aromatic hydrocarbons (e.g., benzene, toluene, xylene, etc.), saturated hydrocarbons (e.g., hexane, heptane, cyclohexane, etc.), ethers (e.g., diethylether, tetrahydrofuran, dioxane, dimethoxyethane, etc.), ketones (e.g., acetone, methylethylketone, etc.) and the like.

This reaction may be performed usually at a temperature of about 0 to 150° C., preferably about 20 to 80° C., and the reaction time is usually about 1 to 10 hours, preferably about 2 to 4 hours.

Said deprotection in the case where a protective group represented by M is an optionally substituted $C_{6-10}$ arylsulfonyl group may employ a treatment with an acid, thereby cleaving said protective group.

Examples of an acid to be employed are organic acids (e.g., formic acid, acetic acid, etc.) and inorganic acids (e.g., hydrobromic acid, sulfuric acid, hydrochloric acid, etc.).

Examples of a solvent employed in said reaction are those employed in the hydrolysis described above as well as phenols.

This reaction may be performed usually at a temperature of about 0 to 150° C., preferably about 20 to 80 ° C., and the reaction time is usually about 1 to 10 hours, preferably about 2 to 4 hours.

When a protective group represented by M is an optionally substituted $C_{1-4}$ alkyloxycarbonyl group, said protective group may be cleaved by a reaction such as a catalytic hydrogenation described above, a hydrolysis described above, as well as a reaction employing an alkylsilyl reagent (e.g., iodotrimethylsilane, triethylsilane, etc.) and a reaction employing a Lewis acid (e.g., aluminum chloride, boron tribromide, boron trifluoride-ethyl ether complex, etc.).

Examples of a solvent employed in a reaction employing an alkylsilyl reagent are aromatic hydrocarbons (e.g., benzene, toluene, xylene, etc.), halogenated hydrocarbons (e.g., carbon tetrachloride, 1,2-dichloroethane, dichloromethane, chloroform, etc.), saturated hydrocarbons (e.g., hexane, heptane, cyclohexane, etc.), ethers (e.g., diethylether, tetrahydrofuran, dioxane, dimethoxyethane, etc.), ketones (e.g., acetone, methylethylketone, etc.), nitrites (e.g., acetonitrile, etc.), sulfoxides (e.g., dimethylsulfoxide, etc.), amides (N,N-dimethylformamide, N,N-dimethylacetoamide, etc.), esters (e.g., ethyl acetate, etc.), pyridine, dimethoxyethane and the like.

The amount of an alkylsilyl reagent to be used is preferably about 1 to 10 mole equivalents, more preferably about 1 to 3 moles, per 1 mole of a starting compound.

This reaction may be performed usually at a temperature of about −20 to 50° C., preferably about 0 to 25° C., and the reaction time is usually about 1 to 24 hours, preferably about 2 to 4 hours.

Examples of a solvent employed in said reaction employing a Lewis acid are those employed in a reaction employing an alkylsilyl reagent described above.

The amount of a Lewis acid to be used is preferably about 1 to 10 mole equivalents, more preferably about 1 to 3 moles, per 1 mole of a starting compound.

This reaction may be performed usually at a temperature of about −40 to 150° C., preferably about −10 to 40° C., and the reaction time is usually about 1 to 24 hours, preferably about 2 to 6 hours.

Compound (I-2) thus obtained may be isolated and purified by a known separation and isolation method such as concentration, concentration under reduced pressure, solvent extraction, crystallization, recrystallization, partition, chromatography and the like.

Acylation producing compound (I-3) from compound (I-2) indicated in Scheme 2 shown below may for example be performed as illustrated below.

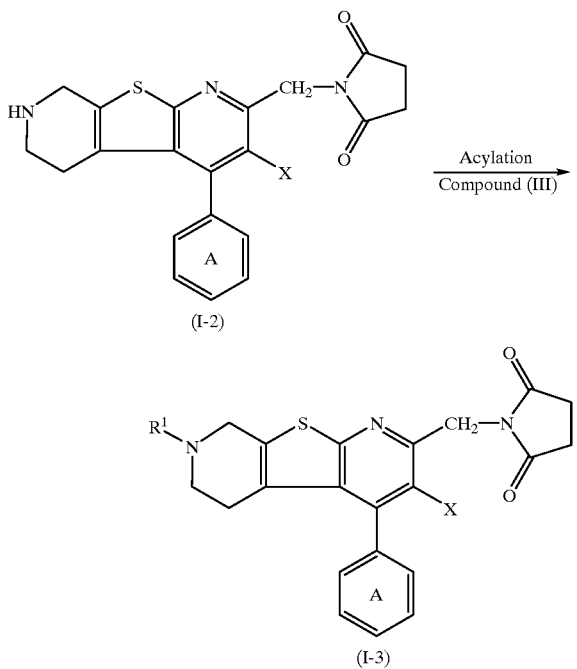

(I-2)

(I-3)

wherein each symbol is the same as defined above.

In this method, compound (I-2) is reacted with compound of the formula (III):

$$R^1—COOH \qquad (III)$$

wherein $R^1$ is defined as described above or a derivative thereof which is derivatized on its carboxylic acid or a salt thereof, to produce compound (I-3).

A preferred reactive derivative of compound (III) which is derivatized on its carboxylic acid includes an acid halide, an acid anhydride, an activated amide, an activated ester and the like.

Preferred examples of such reactive derivatives are acid chlorides; acid azides; mixed acid anhydrides with substituted phosphoric acids such as, for example, a dialkylphosphoric acid, phenylphosphoric acid, diphenylphosphoric acid, dibenzylphosphoric acid, a halogenated phosphoric acid, a dialkylphosphorous acid, sulfurousacid, thiosulfuricacid, sulfuricacid, sulfonic; acids such as methanesulfonic acid, aliphatic carboxylic acids such as acetic acid, propionic acid, butyric acid, isobutyric acid, pivalic acid, pentanoic acid, isopentanoic acid, trichloroacetic acid and the like or an, aromatic carboxylic acid such as benzoic acid; symmetric: acid anhydrides; activated amides with imidazol, 4-substituted imidazole, dimethylpyrazole, triazole and tetrazole; or activated esters such as cyanomethylester, methoxymethylester, dimethyliminomethylester, vinylester, propargylester, p-nitrophenylester, trichlorophenylester, pentachlorophenylester, mesylphenylester, phenylazophenylester, phenylthioester, p-cresylthioester, carboxymethylthioester, pyranylester, pyridylester, piperidylester, 8-guinolylthioester and the like; or esters with N-hydroxy compounds such as N,N-dimethylhydroxyamine, 1-hydroxy-2-(1H)-pyridone, N-hydroxysuccinimide, N-hydroxyphthalimide, 1-hydroxy- 1H-benzotriazole and the like.

Selection from these reactive derivatives may depend on the types of compound (III) employed. A preferable salt of a reactive derivative of compound (III) includes base salts such as alkaline metal salts such as sodium salts, potassium salts and the like, alkaline earth metal salts such as calcium salts, magnesium salts and the like, ammonium salts, organic base salts such as trimethylamine salts, triethylamine salts, pyridine salts, picoline salts, dicyclohexylamine salts, N,N-dibenzylethylenediamine salts and the like.

The reaction may be conducted usually in water, an alcohol such as methanol, ethanol and the like, an ordinary solvent such as acetone, dioxane, acetonitrile, chloroform, methylene chloride, ethylene chloride, tetrahydrofurane, ethyl acetate, N,N-dimethylformamide, pyridine and the like, while the reaction may be conducted in any other organic solvent provided that the reaction is not affected adversely. Such ordinary solvent may be used in a mixture with water. In this reaction, when compound (III) is employed as a free acid or a salt thereof, then the reaction may preferably be conducted in the presence of an ordinary condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide, N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoryacetylene; 1-alkoxy-1-chloroethylene; trialkyl phosphite; ethyl polyphosphate; isopropyl polyphosphate; phosphorus oxychloride; diphenylphosphoryl azide; thionyl chloride; oxalyl chloride; a lower alkyl haloformic acid such as ethyl chloroformate and isopropyl chloroformate; triphenylphosphine; 2-ethyl-7-hydroxybenzisooxazolium salt, 2-ethyl-5-(m-sulfonyl)isooxazolium hydroxide inner salt; N-hydroxybenzotriazole; 1-(p-chlorobenzenesulfonyloxy)-6-chloro-1H-benzotriazole; a Vilsmeier reagent prepared by reaction of N,N-dimethylformamide with thionyl chloride, phosgene, trichloromethyl chloroformate, and the like. The reaction may also be conducted in the presence of an inorganic base or an organic base such as hydrogen carbonate of alkaline metals, tri(lower )alkylamines, pyridine, N-(lower)-alkylmorpholines, N,N-di(lower)alkylbenzylamines and the like.

While the reaction temperature is not particularly limited, the reaction is conducted usually under the condition of from cooling (about –40° C.) to warming (about 150° C.) condition. Preferably its range is from about –20° C. to 60° C. The reaction time may be about 1 to 24 hours, preferably about 2 to 6 hours.

Compound (I-3) thus obtained may be isolated and purified by a known separation and isolation method such as concentration, concentration under reduced pressure, crystallization, solvent extraction recrystallization, partition, chromatography and the like.

A starting compound (II) employed for producing compound (I-2) may be produced by a method such as those disclosed in Japanese Patent Application Laid-Open No.10-36374 or PCT International Application Laid-Open No.WO97/40050 as well as methods equivalent thereto.

As compound (I) or a salt thereof of the present invention has anti-inflammatory activity and also anti-arthritic activity, it can be used for preventing or treating any arthritic symptoms, e.g., arthritic, which exhibits inflammation at a joint. Examples of said arthritis are chronic rheumatoid arthritis and the like.

Compound (I) or a salt thereof can be also used for preventing or treating rheumatism and the like.

Compound (I) or a salt thereof is also effectively used for preventing or treating bone destruction, osteoporosis and the like which accompanies with arthritic symptoms, due to its excellent bone resorption inhibitory activity. Further, compound (I) has an activity for inhibiting production of immunocytokines and is useful for preventing or treating immune-related diseases and rejection after organ transplation.

Based upon the above-mentioned activity for inhibiting production of immunocytokines, e.g., interleukin-2 (IL-2) and interferon-γ (IFN-γ), compound (I) or a salt thereof is also useful for preventing or treating immune-related diseases including autoimmune disease.

Examples of the immune-related diseases include systemic lupus erythematosus, inflammatory bowel disease (idiopathic ulcerative colitis, Crohn's disease), multiple sclerosis, psoriasis, chronic hepatitis, bladder carcinoma, breast cancer, cancer of the uterine cervix, chronic lymphocytic leukemia, chronic mylogenous leukemia, carcinoma of the colon and rectum, colonic cancer, rectal cancer, *Helicobacter pylori* bacterial infectious disease, Hodgkin's disease, insulin dependent diabetes mellitus, malignant melanoma, multiple myeloma, non-Hodgkin's lymphoma, non-small cell lung cancer, ovarian cancer, peptic ulcer, prostatic cancer, septic shock, tuberculosis, sterility, arteriosclerosis, Bechet's disease, asthma, atopic dermatitis, nephritis, systemic fungal infection, acute bacterial meningitis, acute myocardial infarction, acute pancreatitis, acute viral encephalitis, adult respiratory distress syndrome, bacterial pneumonia, chronic pancreatitis, herpes simplex virus infection, varicellazoster viral infectious disease, AIDS, human papilloma viral infections disease, influenza, invasive staphylococcal infectious disease, peripheral vessel disease, sepsis, interstitial hepatic disease, and regional ileitis. Especially, compound (I) or a salt thereof is useful for preventing or treating systemic lupus erythematosus, chronic hepatitis, interstitial hepatic disease, asthma, psoriasis, idiopathic ulcerative colitis, Crohn's disease, regional ileitis or multiple sclerosis.

Compound (I) or a salt thereof is useful for preventing or treating rejection after organ transplation.

Compound (I) or a salt thereof shows low toxicity.

Accordingly, compound (I) or a salt thereof is used for preventing or treating inflammatory disease, arthritis, rheumatism, chronic rheumatoid arthritis, autoimmune disease or rejection after organ transplation in mammals including humans (e.g., humans, horses, bovines, swines, dogs, cats, rats, mice, etc.). Compound (I) is stable to metabolism in a body, so that it can show its phamacological efficacy continuously for a long time. This is a preferable feature for a medicinal substance.

The dose of compound (I) or a salt thereof used in the present invention is variable according to route of administration and symptoms of the subject patient. It can be chosen over the range from, for example, about 1 mg to about 500 mg, preferably from about 5 mg to about 100 mg, more preferably from about 10 mg to about 50 mg, for oral administration. The range from about 1 mg to about 30 mg is also appreciable for oral administration. The dose range from about 0.1 mg to about 100 mg, preferably front about 0.3 mg to about 10 mg, for non-oral administration. These daily doses are for each adult, and may be administered in 1 to 3 portions dividedly.

Compound (I) or a salt thereof of the present invention can be administered orally or non-orally, as formulated with a pharmaceutically acceptable carrier, in the form of solid preparations such as tablets, capsules, granules and powders, or liquid preparations such as syrups and injectable preparations. Alternatively, it can be in the form of preparation for transdermal administration, e.g., a patch, a cataplasm, an ointment (including a cream), an emplastrum, a tape, a lotion, a liquid preparation, a suspension, an emulsion, a nebulizing preparation and the like.

Pharmaceutically acceptable carriers are various organic or inorganic carrier substances in common use as pharmaceutical materials. They include excipients, lubricants, binders and disintegrants for solid preparations; and solvents, dissolution aids, suspending agents, isotonizing agents, buffers and soothing agents for liquid preparations. Other pharmaceutical additives such as preservatives, antioxidants, stabilizing agents, coloring agents and sweetening agents may be used as necessary.

Preferable excipients include lactose, sucrose, D-mannitol, starch, crystalline cellulose and light silicic anhydride.

Preferable lubricants include magnesium stearate, calcium stearate, talc and colloidal silica.

Preferable binders include crystalline cellulose, pregelatinized starch, sucrose, D-mannitol, dextrin, hydroxypropyl cellulose, hydroxypropylmethyl cellulose and polyvinylpyrrolidone. Preferable disintegrants include starch, carboxymethyl cellulose, carboxymethyl cellulose calcium, croscarmellose sodium and carboxymethyl starch sodium, low-substituted hydroxypropyl cellulose. Preferable solvents include water for injection, alcohol, propylene glycol, macrogol, sesame oil and corn oil.

For the purpose of the masking of its taste, enteric-coated preparation or sustained-release preparation, boating by per se known method can be applied to obtain such a preparation for an oral administration. Examples of the coating agents include hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethylcelullose acetate succinate, Eudragit (Rhom, Doyl, methacrylic acid-acrylic acid copolymer).

Preferable dissolution aids include polyethylene glycol, propylene glycol, D-mannitol, benzyl benzoate, ethanol, tris-aminomethane, cholesterol, triethanolamine, sodium carbonate, sodium citrate and the like. Preferable suspending agents include surfactants such as stearyltriethanolamine, sodium lauryl sulfate, lauryl-aminopropionic acid, lecithin, benzalkonium chloride, benzethonium chloride and monostearic glycerol; and hydrophilic polymers such as polyvinyl alcohol, polyvinylpyrrolidone, carboxymethyl cellulose sodium, methyl cellulose, hydroxymethyl cellulose, hydroxyethyl cellulose, hydroxypropyl cellulose and the like. Preferable isotonizing agents include sodium chloride, glycerol, D-mannitol and the like. Preferable buffers include buffer solutions of phosphates, acetates, carbonates, citrates and the like. Preferable soothing agents include benzyl alcohol and the like. Preferable preservatives include p-hydroxybenzoic acid esters, chlorobutanol, benzyl alcohol, phenethyl alcohol, dehydroacetic acid, sorbic acid and the like. Preferable antioxidants include sulfites, ascorbic acid and the like.

Compound (I) or a salt thereof can be administered together with compounds excluding the compound according to the present invention, such as ① cyclooxygenase inhibitors (Cox-I or Cox-II suppressant), ② disease modifying antirheumatic drugs and immunosuppressant, ③ antibodies, soluble receptors and receptor antagonists, ④ analgesics and anti-inflammatory agents or ⑤ the agents for treating or preventing bone diseases etc. at the sames time or at the independent having interval.

① Examples of cyclooxygenase inhibitors (Cox-I or Cox-II suppressant) are celecoxib, rofrcoxib, salicylate derivatives (e.g. aspirin), diclofenac, indomethacin, loxoprofen, and the like. The dose of cyclooxygenase inhibitors is, for example, about 10 to 30 mg/day in case of celecoxib, rofrcoxib, about 1000 to 4500 mg/day in case; of salicylate derivatives (e.g. aspirin), about 25 to 75 mg/day in case of diclofenac, about 50 to 150 mg/days in case of indomethacin, about 60 to 180 mg/day in case of loxoprofen.

② Examples of disease modifying antirheumatic drugs and immunosuppressants are methotrexate, leflunomide, tacrolimus, sulphasalazine, D-penicillamine, gold sodium thiomalate, and the like. The dose of disease modifying antirheumatic drugs and immunosuppressant is, for example, about 2.5 to 7.5 mg/week in case of methotrexate, about 20 to 100 mg/day in case of leflunomide, about 1 to 5 mg/day in case of tacrolimus, about 500 to 2000 mg/day in case of sulfasalazine, about 100 to 600 mg/day in case of D-penicillamine, about 3 to 6 mg/day in case of gold sodium thiomalate.

③ (Examples of antibodies, soluble receptors and receptor antagonists are monoclonal antibodies (e.g. anti-TNF-α antibody, anti-IL-12 antibody, anti-IL-6 antibody, anti-ICAM-I antibody, anti-CD4 antibody etc.), soluble receptor (e.g. soluble TNF-a receptor etc.), receptor antagonist (e.g. IL-1 receptor antagonist etc.). The dose of antibodies, soluble receptors and receptor antagonists is, for example about 0.1 to 50 mg/kg/day, preferably about 0.5 to 20 mg/kg/day.

④ Examples of analgesics and anti-inflammatory agents are central analgesics (e.g. morphine, codeine, pentazocine etc. ), steroids (predonisolone, dexamethasone, betamethasone etc,), anti-inflammatory enzyme agents (e.g. bromelins, lysozyme, etc.), and the like. The dose of analgesics and anti-inflammatory agents is, for example about 1 to 1000 mg/day, preferably about 5 to 300 mg/day in case of central analgesics; for example about 0.1 to 400 mg/day, preferably about 0.5 to 100 mg/day in case of steroids; for example about 1 to 100 mg l day, preferably about 5 to 40 mg/day in case of anti-inflammatory enzyme agents.

⑤ Examples of the agents for treating or preventing bone diseases (e.g., bone fractures, refracture, osteoporosis, osteomalacia, Behcet's syndrome of bone, ankylosing spondylitis, rheumatoid arthritis, and joint tissue destruction caused by deformation gonarthritis and the related diseases) are a formulation of calcium compound (e.g. calcium carbonate), calcitonin, vitamin D (e.g. alfacalcidol), sex hormone (e.g. estrogen, estradiol), prostaglandin $A_1$, bis-phosphonic acid, ipriflavone, fluoride compound (e.g. sodium fluoride), vitamin $K_2$, BMP (bone morphogenetic protein), FGF (fibroblast growth factor), PDGF (platelet derived growth factor), TGF-β (transforming growth factor-β), IGF-1 (insulin like growth factor-1), IGF-2 (insulin like growth factor-2), PTH (parathyroid hormone), a compound described in European Patent Application Laid-Open No. EP-A1-376194, EP-A1-460488 and EP-A1-719782 (e.g. (2R.4S)-(-)-N-[4-(diethoxyphosphorylmethyl)phenyl]-1,2, 4,5-tetrahydro-4-methyl-7,8-methylenedioxy-5-oxo-3-benzothiepin-2-carboxamide, etc.) and the like.

Best Mode for Carrying out the Invention

In the following, the present invention is illustrated specifically by Reference Examples, Examples and Test Examples, but these should by no means be construed as limiting the scope of the invention.

In the following, Me means methyl, Et means ethyl, Ph means phenyl and Cbz means benzyloxycarbonyl respectively.

REFERENCE EXAMPLE 1

Acetonitrile (48 g) was added dropwise to a mixture of 1.6 M solution of n-butyllithium in hexane (728 ml) and tetrahydrofurane (900 ml) at −70° C. After stirring at −70° C. for 20 minutes, a solution of 4-methoxybenzoyl chloride (100 g) in tetrahydrofurane (200 ml) was added dropwise at this temperature. After stirring the reaction mixture for further 30 minutes at the same temperature, the mixture was acidified with 4N hydrochloric acid. After stirring for 30 minutes at room temperature, the precipitated crystal was isolated by filtration to obtain ω-cyano-4-methoxyacetophenone (69.5 g, 68%). The product was recrystallized from ethanol. A colorless prism crystal. M.p. 127 to 128° C.

REFERENCE EXAMPLE 2

Using 3,4-dimethoxybenzoyl chloride as a starting material, ω-cyano-3,4-dimethoxyacetophenone was obtained in the manner similar to that in Reference Example 1. The product was recrystallized from ethyl acetate. A colorless prism crystal. M.p. 141 to 142° C.

REFERENCE EXAMPLE 3

Using ethyl 4-isopentyloxybenzoate as a starting material, ω-cyano-4-isopentyloxyacetophenone was obtained in the manner similar to that in Reference Example 1. The product was recrystallized from isopropylether-hexane. A colorless prism crystal. M.p. 77 to 78° C.

REFERENCE EXAMPLE 4

Using 4-trifluoromethylbenzoyl chloride as a starting material, ω-cyano-4-trifluoromethylacetophenone was obtained as an amorphous solid in the manner similar to that in Reference Example 1.

$^1$H-NMR (δ ppm in $CDCl_3$): 4.11(2H,s), 7.80(2H,d,J=8.6 Hz), 8.05(2H,d,J=8.6 Hz).

REFERENCE EXAMPLE 5

Using 4-t-butylbenzoyl chloride as a starting material, ω-cyano-4-t-butylacetophenone was obtained in the manner similar to that in Reference Example 1. The product was recrystallized from isopropylether-hexane. A colorless sheet crystal. M.p. 74 to 76° C.

REFERENCE EXAMPLE 6

Using ethyl 4-acetylaminobenzoate as a starting material, ω-cyano-4-acetylaminoacetophenone was obtained in the manner similar to that in Reference Example 1. The product was recrystallized from N,N-dimethylformamide-water. A colorless prism crystal. M.p. 255 to 257° C.

REFERENCE EXAMPLE 7

Acetonitrile (4.2 g) was added dropwise to a mixture: of a 1.6 M solution of n-butyllithium in hexane (63 ml) and tetrahydrofurane(200ml)at −70° C. After stirring at −70° C., for 30 minutes, the mixture was added dropwise to a solution of diethyl terephthalate (15 g) in tetrahydrofurane (200 ml) at this temperature. After stirring for further 30 minutes at the same temperature, the mixture was acidified with 2N hydrochloric acid, and extracted with ethyl acetate. The ethyl acetate layer was washed with water, dried ($MgSO_4$), and the solvent was distilled off under reduced pressure. The residue was subjected to column chromatography on silica gel. From a fraction eluted with ethyl acetate-hexane (2:1, v/v), ω-cyano-4-ethoxycarbonylacetophenone (10.5 g, 72%) was obtained. The product was recrystallized from ethyl acetate-hexane. A colorless needle crystal. M.p. 88 to 89° C.

REFERENCE EXAMPLE 8

Using ethyl 4-ethoxybenzoate as a starting material, ω-cyano-4-ethoxyacetophenone was obtained in the manner similar to that in Reference Example 1. The product was recrystallized from methanol. A colorless prism crystal. M.p. 121 to 122° C.

REFERENCE EXAMPLE 9

Using ethyl 4-(2,2,2-trifluoroethoxy)benzoate as a starting material, ω-cyano-4-(2,2,2-trifluoroethoxy) acetophenone was obtained in the manner similar to that in Reference Example 1. The product was recrystallized from ethyl acetate-hexane. A colorless needle crystal. M.p. 116 to 117° C.

REFERENCE EXAMPLE 10

Using ethyl 4-ethylbenzoate as a starting material, ω-cyano-4-ethylacetophenone was obtained in the manner similar to that in Reference Example 1. The product was recrystallized from methanol. A colorless prism crystal. M.p. 97 to 98° C.

REFERENCE EXAMPLE 11

Using ethyl 4-benzyloxybenzoate as a starting material, ω-cyano-4-benzyloxyacetophenone was obtained in the manner similar to that in Reference Example 1. Thee product was recrystallized from methanol. A colorless prism crystal. M.p. 127 to 128° C.

REFERENCE EXAMPLE 12

A mixture of the compound obtained in Reference Example 1 (40 g), sulfur (8 g), 1-benzyl-4-piperidone (43.2 g), morpholine (19.9 g) and 2-propanol (1000 ml) was stirred for 5 hours at 70° C. The reaction mixture was allowed to stand at room temperature overnight. The precipitated crystal was isolated by filtration, washed with 2-propanol to obtain 2-amino-6-benzyl-3-(4-methoxybenzoyl)-4,5,6,7-tetrahydrothieno[2,3-c]pyridine (52.4 g, 61%). The product was recrystallized from ethyl acetate-hexane. A yellow prism crystal. M.p. 164 to 165° C.

REFERENCE EXAMPLE 13

Using the compound obtained in Reference Example 2 as a starting material, 2-amino-6-benzyl-3-(3,4-dimethoxybenzoyl)-4,5,6,7-tetrahydrothieno[2,3-c]pyridine was obtained in the manner similar to that in Reference Example 12. The product was recrystallized from ethanol. A yellow prism crystal. M.p. 149 to 150° C.

REFERENCE EXAMPLE 14

Using the compound obtained in Reference Example 3 as a starting material, 2-amino-6-benzyl-4,5,6,7-tetrahydro-3-(4-isopentyloxybenzoyl)thieno[2,3-c]pyridine was obtained in the manner similar to that in Reference Example 12. The product was recrystallized from ethyl acetate-hexane. A yellow prism crystal. M.p. 106 to 107° C.

REFERENCE EXAMPLE 15

Using the compound obtained by the method described in Reference Example 24 in JP-A-59977/1998 as a starting material, 2-amino-6-benzyl-3-(4-chlorobezoyl)-4,5,6,7-tetrahydrothieno[2,3-c]pyridine was obtained in the manner similar to that in Reference Example 12. The product was recrystallized from tetrahydrofuran-hexane. A yellow needle crystal. M.p. 158 to 159° C.

REFERENCE EXAMPLE 16

Using the compound obtained in Reference Example 5 as a starting material, 2-amino-6-benzyl-3-(4-t-butylbenzoyl)-4,5,6,7-tetrahydrothieno[2,3-c]pyridine was obtained in the manner similar to that in Reference Example 12. The product was recrystallized from ethyl acetate-hexane. A yellow prism crystal. M.p. 124 to 125° C.

REFERENCE EXAMPLE 17

Using the compound obtained by the method described in Reference Example 22 in JP-A-59977/1998 as a starting material, 2-amino-6-benzyl-4,5,6,7-tetrahydro-3-(4-isopropylbenzoyl)thieno[2,3-c]pyridine was obtained in the manner similar to that in Reference Example 12. The product was recrystallized from ethyl acetate-hexane. A yellow prism crystal. M.p. 157 to 158 ° C.

REFERENCE EXAMPLE 18

Using the compound obtained in Reference Example 6 as a starting material, 2-amino-3-(4-acetylaminobenzoyl)-6-benzyl-4,5,6,7-tetrahydrothieno[2,3-c]pyridine was obtained in the manner similar to that in Reference Example 12. The product was recrystallized from ethyl acetate-hexane. A yellow needle crystal. M.p. 119 to 120° C.

REFERENCE EXAMPLE 19

Using the compound obtained in Reference Example 7 and 1-benzyloxycarbonyl-4-piperidone as starting materials, 2-amino-6-benzyloxycarbonyl-3-(4-ethoxycarbonylbenzoyl)-4,5,6,7-tetrahydrothieno[2,3-c] pyridine was obtained in the manner similar to that in Reference Example 12. The product was recrystallized from tetrahydrofuran-ethyl acetate. A yellow needle crystal. M.p. 195 to 196° C.

REFERENCE EXAMPLE 20

Using the compound obtained in Reference Example 8 and 1-benzyloxycarbonyl-4-piperidone as starting materials, 2-amino-6-benzyloxycarbonyl-3-(4-ethoxybenzoyl)-4,5,6,7-tetrahydrothieno[2,3-c]pyridine was obtained in the manner similar to that in Reference Example 12. The product was recrystallized from tetrahydrofuran-ethylacetate. A color less prism crystal. M.p. 197 to 198° C.

REFERENCE EXAMPLE 21

Using the compound obtained in Reference Example 9 and 1-benzyloxycarbonyl-4-piperidone as starting materials, 2-amino-6-benzyloxycarbonyl-4,5,6,7-tetrahydro-3-[4-(2,2,2-trifluoroethoxy)benzoyl)]thieno[2,3-c]pyridine was obtained in the manner similar to that in Reference Example 12. The product was recrystallized from ethyl acetate-hexane. A yellow prism crystal. M.p. 146 to 147° C.

REFERENCE EXAMPLE 22

Using the compound obtained in Reference Example 10 and 1-benzyloxycarbonyl-4-piperidone as starting materials. 2-amino-6-benzyloxycarbonyl-3-(4-ethylbenzoyl)-4,5,6,7-tetrahydrothieno[2,3-c]pyridine was obtained in the manner similar to that in Reference Example 8. The product was recrystallized from ethyl acetate. A yellow prism crystal. M.p. 121 to 123° C.

REFERENCE EXAMPLE 23

Using the compound obtained in Reference Example 11 and 1-benzyloxycarbonyl-4-piperidone as starting materials, 2-amino-6-benzyloxycarbonyl-3-(4-benzyloxybenzoyl)-4,5,6,7-tetrahydrothieno[2,3-c]pyridine was obtained in the manner similar to that in Reference Example 12. The product was recrystallized from ethyl acetate-hexane. A yellow prism crystal. M.p. 151 to 152° C.

REFERENCE EXAMPLE 24

To a mixture of the compound obtained in Reference Example 12 (8 g), 1,3-dichloroacetone (5.4 g) and tetrahydrofurane (140 ml) was added aluminum chloride (6.5 g) while cooling with ice, and then the mixture was refluxed for 2.5 hours. The reaction mixture was poured onto toluene (100 ml)-water (100 ml) with stirring. After washing the toluene layer followed by drying (MgSO$_4$), the solvent was distilled off under reduced pressure. 7-Benzyl-3-chloro-2-chloromethyl-5,6,7,8-tetrahydro-4-(4-methoxyphenyl)thieno[2,3-b:5,4-c']dipyridine (8.2 g, 83%) was obtained. The product was recrystallized from ethanol. M.p. 194 to 195° C.

REFERENCE EXAMPLE 25

Using the compound obtained in Reference Example 13 as a starting material, 7-benzyl-3-chloro-2-chloromethyl-4-(3,4-dimethoxyphenyl)-5,6,7,8-tetrahydrothieno[2,3-b:5,4-c']dipyridine was obtained in the manner similar to that in Reference Example 24. The product was recrystallized from ethyl acetate-hexane. A colorless prism crystal. M.p. 171 to 172 ° C.

REFERENCE EXAMPLE 26

Using the compound obtained in Reference Example 14 as a starting material, 7-benzyl-3-chloro-2-chloromethyl-5,6,7,8-tetrahydro-4-(4-isopentyloxyphenyl)thieno[2,3-b:5,4-c']dipyridine was obtained in the manner similar to that in Reference Example 24. The product was recrystallized from tetrahydrofuran-hexane. A colorless prism crystal. M.p. 149 to 150° C.

REFERENCE EXAMPLE 27

Using the compound obtained in Reference Example 12 and 1,3-dibromoacetone as starting materials, 7-benzyl-3-bromo-2-bromomethyl-5,6,7,8-tetrahydro-4-(4-methoxyphenyl)thieno[2,3-b:5,4-c']dipyridine was obtained in the manner similar to that in Reference Example 24. The product was recrystallized from tetrahydrofuran-hexane. A colorless prism crystal. M.p. 177 to 178° C.

REFERENCE EXAMPLE 28

Using the compound obtained in Reference Example 15 as a starting material, 7-benzyl-3-chloro-2-chloromethyl-4-(4-chlorophenyl)-5,6,7,8-tetrahydrothieno[ 2,3-b:5,4-c']dipyridine was obtained in the manner similar to that in Reference Example 24. The product was recrystallized from tetrahydrofuran-hexane. A colorless prism crystal. M.p. 204 to 205° C.

REFERENCE EXAMPLE 29

A mixture of the compound obtained in Reference Example 4 (8.3 g), 1-benzyloxycarbonyl-4-piperidone (10 g), sulfur (1.3 g), morpholine (3.4 g) and isopropanol (200ml) was stirred for 6 hours at 60° C., and then concentrated under reduced pressure. The residue was subjected to column chromatography. The fraction eluted with ethyl acetate-hexane (1:1, v/v) was collected and concentrated. To the residue thus obtained (5 g) and 1,3-dichloroacetone, (2.8 g) dissolved in tetrahydrofuran (100 ml), aluminum chloride (3.3 9) was added at room temperature, and then the mixture was refluxed for 2hours. The reaction solution was poured onto toluene (100 ml)-water (50 ml). After washing the toluene layer with water and saturated brine followed by drying (MgSO$_4$), the solvent was distilled off under reduced pressure. The residue was subjected to column chromatography on silica gel. From a fraction eluted with hexane-ethyl acetate-chloroform (2:1:1, v/v), 7-benzyloxycarbonyl-3-chloro-2-chloromethyl-4-(4-trifluoromethylphenyl)[2,3-b:5,4-c']dipyridine was obtained (2.2 g, 14%). The product was recrystallized from ethyl acetate-hexane. A colorless prism crystal. M.p. 146 to 147° C.

REFERENCE EXAMPLE 30

Using the compound obtained in Reference Example 16 as a starting material, 7-benzyl-4-(4-t-butylphenyl)-3-chloro-2-chloromethyl-5,6,7,8-tetrahydrothieno[2,3-b:5,4-c']dipyridine was obtained in the manner similar to that in Reference Example 24. The product was recrystallized from tetrahydrofuran-hexane. A colorless prism crystal. M.p. 208 to 209° C.

REFERENCE EXAMPLE 31

Using the compound obtained in Reference Example 17 as a starting material, 7-benzyl-3-chloro-2-chloromethyl-5,6,7,8-tetrahydro-4-(4-isopropylphenyl)thieno[2,3-b:5,4-c']dipyridine was obtained in the manner similar to that in Reference Example 24. The product was recrystallized from ethyl acetate-hexane. A colorless prism crystal. M.p. 190 to 192° C.

REFERENCE EXAMPLE 32

Using the compound obtained in Reference Example 18 as a starting material, 4-(4-acetylaminophenyl)-7-benzyl-3-chloro-2-chloromethyl-5,6,7,8-tetrahydrothieno[2, 3-b: 5,4-c']dipyridine was obtained in the manner similar to that in Reference Example 24. The product was recrystallized from tetrahydrofuran-hexane. A colorless prism crystal. M.p. 203 to 204° C.

REFERENCE EXAMPLE 33

Using the compound obtained in Reference Example 19 as a starting material, 7-benzyloxycarbonyl-3-chloro-2-chloromethyl-4-(4-ethoxycarbonylphenyl)-5,6,7,8-tetrahydrothieno[2,3-b:5,4-c']dipyridine was obtained in the manner similar to that in Reference Example 24. The product was recrystallized from ethyl acetate-hexane. A colorless prism crystal. M.p. 123 to 124° C.

REFERENCE EXAMPLE 34

A mixture of the compound obtained in Reference Example 20 (30 g), 1,3-dichloroacetone (15.7 g), p-toluenesulfonic acid monohydrate (3.9 g), benzene (500 ml) was heated under reflux for 3 hours. The reaction mixture was washed successively with saturated aqueous sodium bicarbonate and water, dried (MgSO$_4$) and concentrated under reduced pressure. The residue was subjected to column chromatography on silica gel to obtain 7-benzyloxycarbonyl-3-chloro-2-chloromethyl-4-(4-ethoxyphenyl)-5,6,7,8-tetrahydrothieno[2,3-b:5,4-c'] dipyridine (21 g, 58%) from a fraction eluted with ethyl acetate-hexane (1:10, v/v). The product was recrystallized from ethyl acetate. A colorless prism crystal. M.p. 159 to 161° C.

REFERENCE EXAMPLE 35

Using the compound obtained in Reference Example 21 as a starting material, 7-benzyloxycarbonyl-3-chloro-2-chloromethyl-5,6,7,8-tetrahydro-4-[4-(2,2,2-trifluoroethoxy)phenyl]thieno[2,3-b:5,4-c']dipyridine was obtained in the manner similar to that in References Example 24. The product was recrystallized from ethyl acetate-hexane. A colorless prism crystal. M.p. 166 to 167° C.

REFERENCE EXAMPLE 36

Using the compound obtained in Reference Example 22 as a starting material, 7-benzyloxycarbonyl-3-chloro-2-chloromethyl-4-(4-ethylphenyl)-5,6,7,8-tetrahydrothieno[2,3-b:5,4-c']dipyridine was obtained in the manner similar to that in Reference Example 24. The product was recrystallized from ethyl acetate. A colorless prism crystal. M.p. 126 to 128° C.

REFERENCE EXAMPLE 37

Using the compound obtained in Reference Example 23 as a starting material, 7-benzyloxycarbonyl-4-(4-benzyloxyphenyl)-3-chloro-2-chloromethyl- 5,6,7,8-tetrahydrothieno[2,3-b:5,4-c']dipyridine was obtained in the manner similar to that in Reference Example 24. The product was recrystallized from ethyl acetate-hexane. A, colorless prism crystal. M.p. 144 to 145° C.

REFERENCE EXAMPLE 38

A mixture of the compound obtained in Reference Example 24 (13.9 g), succinimide (4.4 g), potassium carbonate (6.2 g) and N,N-dimethylformamide (140 ml) was stirred for 2 hours at 70° C. and then poured onto water and extracted with ethyl acetate. After washing the ethyl acetate layer with water followed by drying ($MgSO_4$), the mixture was concentrated under reduced pressure. The residue was subjected to column chromatography on silica gel to obtain 7-benzyl-3-chloro-5,6,7,8-tetrahydro-4-(4-methoxyphenyl)-2-(succinimidomethyl)thieno[2,3-b:5,4-c']dipyridine (21 g, 58%) from a fraction eluted with ethyl acetate-hexane (1:1, v/v). The product was recrystallized from tetrahydrofuran-isopropylether. A colorless prism crystal. M.p. 241 to 243° C.

REFERENCE EXAMPLE 39

Using the compound obtained in Reference Example 25 as a starting material, 7-benzyl-3-chloro-4-(3,4-dimethoxyphenyl)-5,6,7,8-tetrahydro-2-(succinimidomethyl)thieno[2,3-b:5,4-c']dipyridine was obtained in the manner similar to that in Reference Example 38. The product was recrystallized from ethanol-hexane. A colorless prism crystal. M.p. 128 to 130° C.

REFERENCE EXAMPLE 40

Using the compound obtained in Reference Example 26 as a starting material, 7-benzyl-3-chloro-5,6,7,8-tetrahydro-4-(4-isopentyloxyphenyl)-2-(succinimidomethyl)thieno[2,3-b:5,4-c']dipyridine was obtained as an amorphous solid in the manner similar to that in Reference Example 38.

$^1$H-NMR($\delta$ppm in $CDCl_3$): 0.99(6H,d,J=6.6 Hz), 1.72 (2H,q,J=6.6 Hz), 1.78–2.02 (3H,m), 2.54(2H, t,J=5.4 Hz), 2.91(4H,s), 3.64(2H,s), 3.68(2H,s), 4.04(2H,t, J=6.6 Hz), 5.02(2H,s), 6.96(2H,d,J=8.8Hz), 7.12(2H,d,J=8.8Hz), 7.20–7.41(5H,m).

REFERENCE EXAMPLE 41

Using the compound obtained in Reference Example 27 as a starting material, 7-benzyl-3-bromo-5,6,7,8-tetrahydro-4-(4-methoxyphenyl)-2-(succinimidomethyl)thieno[2,3-b:5,4-c']dipyridine was obtained in the manner similar to that in Reference Example 38. The product was recrystallized from ethyl acetate-hexane. A colorless prism crystal. M.p. 255 to 256° C.

REFERENCE EXAMPLE 42

Using the compound obtained in Reference Example 28 as a starting material, 7-benzyl-3-chloro-4-(4-chlorophenyl)-5,6,7,8-tetrahydro-2-(succinimidomethyl)thieno[2,3-b:5,4-c']dipyridine was obtained in the manner similar to that in Reference Example 38. The product was recrystallized from tetrahydrofuran-hexane. A colorless prism crystal. M.p. 254 to 255° C.

REFERENCE EXAMPLE 43

Using the compound obtained in Reference Example 29 as a starting material, 7-benzyloxycarbonyl-3-chloro-5,6,7,8-tetrahydro-2-(succinimidomethyl)-4-(4-trifluoromethylphenyl)thieno[2,3-b:5,4-c']dipyridine was obtained in the manner similar to that in Reference Example 38. The product was recrystallized from ethyl acetate-hexane. A colorless prism crystal. M.p. 201 to 202° C.

REFERENCE EXAMPLE 44

Using the compound obtained in Reference Example 30 as a starting material, 7-benzyl-4-(4-t-butylphenyl)-3-chloro-5,6,7,8-tetrahydro-2-(succinimidomethyl)thieno[2,3-b:5,4-c']dipyridine was obtained in the manner similar to that in Reference Example 38. The product was recrystallized from ethyl acetate-hexane. A colorless prism crystal. M.p. 198 to 199° C.

REFERENCE EXAMPLE 45

Using the compound obtained in Reference Example 31 as a starting material, 7-benzyl-3-chloro-5,6,7,8-tetrahydro-2-(succinimidomethyl)-4-(4-isopropylphenyl)thieno[2,3-b:5,4-c']dipyridine was obtained in the manner similar to that in Reference Example, 38. The product was recrystallized from ethyl acetate-hexane. A colorless prism crystal. M.p. 201 to 202° C.

REFERENCE EXAMPLE 46

Using the compound obtained in Reference Example 32 as a starting material, 4-(4-acethyl aminophenyl)-7-benzyl-3-chloro-5,6,7,8-tetrahydro-2-(succinimidomethyl)thieno[2,3-b:5,4-c']dipyridine was obtained in the manner similar to that in Reference Examples 38. The product was recrystallized from N,N-dimethylformamide-water. A color less prism crystal. M.p. 272 to 273° C.

REFERENCE EXAMPLE 47

Using the compound obtained in Reference Example 33 as a starting material, 7-benzyloxycarbonyl-3-chloro-4-(4- ethoxycarbonylphenyl)-5,6,7,8-tetrahydro-2-(succinimidomethyl)thieno[2,3-b:5,4-c']dipyridine was obtained in the manner similar to that in Reference Example 38. The product was recrystallized from ethyl acetate-hexane. A colorless prism crystal. M.p. 198 to 199° C.

REFERENCE EXAMPLE 48

Using the compound obtained in Reference Example 34 as a starting material, 7-benzyloxycarbonyl-3-chloro-4-(4-ethoxyphenyl)-5,6,7,8-tetrahydro-2-(succinimidomethyl)thienol[2,3-b:5,4-c']dipyridine was obtained in the manner similar to that in Reference Example 38. The product was recrystallized from ethyl acetate. A colorless prism crystal. M.p. 125 to 127° C.

REFERENCE EXAMPLE 49

Using the compound obtained in Reference Example 35 as a starting material, 7-benzyloxycarbonyl-3-chloro-5,6,7,8-tetrahydro-2-(succinimidomethyl)-4-[4-(2,2,2-trifluoroethoxy)phenyl]thieno[2,3-b:5,4-c']dipyridine was obtained in the manner similar to that in Reference Example 38. The product was recrystallized from ethyl acetate-hexane. A colorless prism crystal. M.p. 190 to 191° C.

REFERENCE EXAMPLE 50

Using the compound obtained in Reference Example 36 as a starting material, 7-benzyloxycarbonyl-3-chloro-4-(4-ethylphenyl)-5,6,7,8-tetrahydro-2-(succinimidomethyl)thieno[2,3-b:5,4-c']dipyridine was obtained in the manner similar to that in Reference Example 38. The product was recrystallized from ethyl acetate. A colorless prism crystal. M.p. 170 to 171° C.

REFERENCE EXAMPLE 51

Using the compound obtained in Reference Example 37 as a starting material, 7-benzyloxycarbonyl-4-(4-benzyloxyphenyl)-3-chloro-5,6,7,8-tetrahydro-2-(succinimidomethyl)thieno[2,3-b:5,4-c']dipyridine was obtained in the manner similar to that in Reference Example 38. The product was recrystallized from tetraydrofuran-hexane. A colorless prism crystal. M.p. 238 to 239° C.

REFERENCE EXAMPLE 52

Using the compound obtained by the method described in Reference Example 13 in JP-A-36374/1998 as a starting material, 7-benzyl-3-chloro-5,6,7,8-tetrahydro-4-(4-isoproxy-3-methoxypheny)-2-(succinimifomethyl)thieno[2,3-b:5,4-c']dipyridine was obtained as an amorphous solid in the manner similar to that, in Reference Example 38.

$^1$H-NMR(δppm in CDCl$_3$): 1.43(6H,d,J=6.0 Hz), 1.75–2.08(2H,m), 2.55(2H,t, J=5.2 Hz), 2.91(4H,s), 3.65 (2H,s), 3.67(2H,s), 3.84(3H,s), 4.62(1H,septet, J=6.0 Hz), 5.02(2H,s), 6.68–6.78(2H,m), 6.95(1H,d,J=8.4 Hz), The structures of the compounds obtained in the above Reference Example 1 to 52 are shown in the following Table 1 to Table 6.

TABLE 1

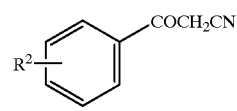

| Reference Example | R$^2$ |
|---|---|
| 1 | 4-MeO |
| 2 | 3-MeO |
|   | 4-MeO |
| 3 | 4-Me$_2$CH(CH$_2$)$_2$O |
| 4 | 4-CF$_3$ |
| 5 | 4-Me$_3$C |
| 6 | 4-CH$_3$CONH |
| 7 | 4-EtOOC |
| 8 | 4-EtO |
| 9 | 4-CF$_3$CH$_2$O |
| 10 | 4-Et |
| 11 | 4-PhCH$_2$O |

TABLE 2

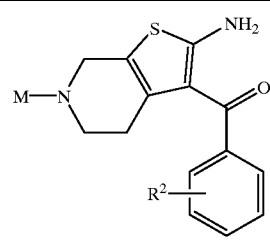

| Reference Example | M | R$^2$ |
|---|---|---|
| 12 | PhCH$_2$ | 4-MeO |
| 13 | PhCH$_2$ | 3-MeO |
|    |          | 4-MeO |
| 14 | PhCH$_2$ | 4-Me2CH(CH$_2$)$_2$O |
| 15 | PhCH$_2$ | 4-Cl |
| 16 | PhCH$_2$ | 4-Me$_3$C |
| 17 | PhCH$_2$ | 4-Me$_2$CH |
| 18 | PhCH$_2$ | 4-CH$_3$CONH |
| 19 | Cbz | 4-EtOOC |
| 20 | Cbz | 4-EtO |
| 21 | Cbz | 4-CF$_3$CH$_2$O |
| 22 | Cbz | 4-Et |
| 23 | Cbz | 4-PhCH$_2$O |

TABLE 3

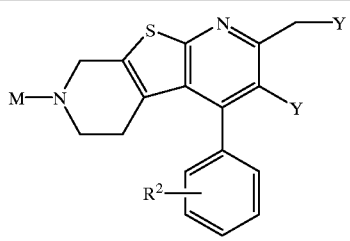

| Reference Example | M | R$^2$ | Y |
|---|---|---|---|
| 24 | PhCH$_2$ | 4-MeO | Cl |
| 25 | PhCH$_2$ | 3-MeO | Cl |
|    |          | 4-MeO |   |
| 26 | PhCH$_2$ | 4-Me$_2$CH(CH$_2$)$_2$O | Cl |
| 27 | PhCH$_2$ | 4-MeO | Br |
| 28 | PhCH$_2$ | 4-Cl | Cl |
| 29 | Cbz | 4-CF$_3$ | Cl |
| 30 | PhCH$_2$ | 4-Me$_3$C | Cl |

TABLE 4

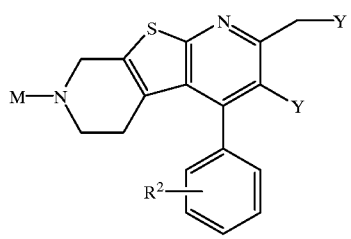

| Reference Example | M | R² | Y |
|---|---|---|---|
| 31 | PhCH₂ | 4-Me₂CH | Cl |
| 32 | PhCH₂ | 4-CH₃CONH | Cl |
| 33 | Cbz | 4-EtOOC | Cl |
| 34 | Cbz | 4-EtO | Cl |
| 35 | Cbz | 4-CF₃CH₂O | Cl |
| 36 | Cbz | 4-Et | Cl |
| 37 | Cbz | 4-PhCH₂O | Cl |

TABLE 5

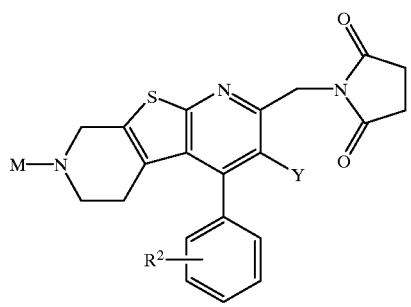

| Reference Example | M | R² | Y |
|---|---|---|---|
| 38 | PhCH₂ | 4-MeO | Cl |
| 39 | PhCH₂ | 3-MeO 4-MeO | Cl |
| 40 | PhCH₂ | 4-Me2CH(CH₂)₂O | Cl |
| 41 | PhCH₂ | 4-MeO | Br |
| 42 | PhCH₂ | 4-Cl | Cl |
| 43 | Cbz | 4-CF₃ | Cl |
| 44 | PhCH₂ | 4-Me₃C | Cl |

TABLE 6

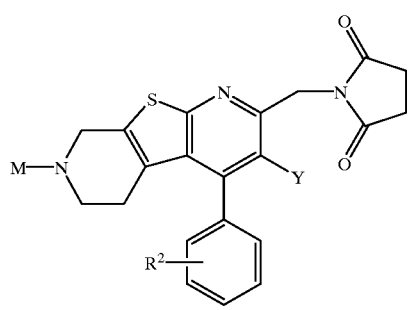

| Reference Example | M | R2 | Y |
|---|---|---|---|
| 45 | PhCH₂ | 4-Me₂CH | Cl |
| 46 | PhCH₂ | 4-CH₃CONH | Cl |
| 47 | Cbz | 4-EtOOC | Cl |
| 48 | Cbz | 4-EtO | Cl |

TABLE 6-continued

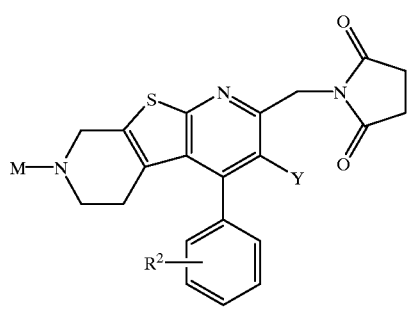

| Reference Example | M | R2 | Y |
|---|---|---|---|
| 49 | Cbz | 4-CF₃CH₂O | Cl |
| 50 | Cbz | 4-Et | Cl |
| 51 | Cbz | 4-PhCH₂O | Cl |
| 52 | PhCH₂ | 3-MeO 4-Me₂CHO | Cl |

EXAMPLE 1

Preparation of 3-chloro-5,6,7,8-tetrahydro-4-(4-methoxyphenyl)-2-(succinimidomethyl)thieno[2,3-b:5,4-c'] dipyridine A mixture of the compound obtained in Reference Example 38 (14.5 g), formic acid (29.1 ml), 10% Pd/C (50% water,14.5 g) and methanol (500 ml) was stirred for 21 hours at room temperature. After filtering the catalyst off, the filtrate was concentrated under reduced pressure. The residue was neutralized with saturated aqueous sodium bicarbonate and the mixture was extracted with ethyl acetate. After washing the ethyl acetate layer with water followed by drying (MgSO₄), the solvent was distilled off and the residue was subjected to column chromatography on silica gel. From a fraction eluted with ethyl acetate-methanol (10:1, v/v), the title compound (5.0 g, 42%) was obtained. The product was recrystallized from ethyl acetate-methanol. A colorless prism crystal. M.p. 225 to 226° C.

EXAMPLE 2

Preparation of 3-chloro-4-(3,4-dimethoxyphenyl)-5,6,7,8-tetrahydro-2-(succinimidomethyl)thieno[2,3-b:5,4-c'] dipyridine Using the compound obtained in Reference Example 39 as a starting material, the title compound was obtained in the manner similar to that in Example 1. The product was recrystallized from tetrahydrofuran-hexane. A colorless prism crystal. M.p. 250 to 252° C.

EXAMPLE 3

Preparation of 3-chloro-5,6,7,8-tetrahydro-4-(4-isopentyloxyphenyl)-2-(succinimidomethyl)thieno[2,3-b:5, 4-c']dipyridine Using the compound obtained in Reference Example 40 as a starting material, the title compound was obtained in the manner similar to that in Example 1. The product was recrystallized from ethyl acetate-hexane. A colorless prism crystal. M.p. 226 to 227° C.

EXAMPLE 4

Preparation of 3-bromo-5,6,7,8-tetrahydro-4-(4-methoxyphenyl)-2-(succinimidomethyl)thieno[2,3-b:5,4-c'] dipyridine Using the compound obtained in Reference Example 41 as a starting material, the title compound was obtained in the manner similar to that in Example 1. The product was recrystallized from ethyl acetate-hexane. A colorless prism crystal. M.p. 219 to 221° C.

EXAMPLE 5
Preparation of 3-chloro-4-(4-chlorophenyl)-5,6,7,8-tetrahydro-2-(succinimidomethyl)thieno[2,3-b:5,4-c'] dipyridine Using the compound obtained in Reference Example 42; as a starting material, the title compound was obtained in the manner similar to that in Example 1. The product was recrystallized from ethyl acetate-hexane. A colorless prism crystal. M.p. 230 to 231° C.

EXAMPLE 6
Preparation of 3-chloro-5,6,7,8-tetrahydro-2-(succinimidomethyl)-4-(4-trifluoromethylphenyl)thienol[2,3-b:5,4-c']dipyridine Using the compound obtained in Reference Example 43 as a starting material, the title compound was obtained in the manner similar to that in Example 1. The product was recrystallized from ethyl acetate-hexane. A colorless prism crystal. M.p. 226 to 227° C.

EXAMPLE 7
Preparation of 4-(4-t-butylphenyl)-3-chloro-5,6,7,8-tetrahydro-2-(succinimidomethyl)thieno[2,3-b:5,4-c'] dipyridine Using the compound obtained in Reference Example 44 as a starting material, the title compound was obtained in the manner similar to that in Example 1. The product was recrystallized from ethyl acetate-hexane. A colorless prism crystal. M.p. 210 to 212° C.

EXAMPLE 8
Preparation of 3-chloro-5,6,7,8-tetrahydro-4-(4-sopropylphenyl)-2-(succinimidomethyl)thieno[2,3-b:5,4-c'] dipyridine Using the compound obtained in Reference Example 45 as a starting material, the title compound was obtained in the manner similar to that in Example 1. The product was recrystallized from ethyl acetate-hexane. A colorless prism crystal. M.p. 204 to 205° C.

EXAMPLE 9
Preparation of 4-(4-acetylaminophenyl)-3-chloro-5,6,7,8-tetrahydro-2-(succinimidomethyl)thieno[2,3-b:5,4-c'] dipyridine Using the compound obtained in Reference Example 46 as a starting material, the title compound was obtained in the manner similar to that in Example 1. The product was recrystallized from tetrahydrofurane-hexane. A colorless prism crystal. M.p. 300° C. or higher.

EXAMPLE 10
Preparation of 3-chloro-4-(4-ethoxycarbonylphenyl)-5,6,7,8-tetrahydro-2-(succinimidomethyl)thieno[2,3-b:5,4-c'] dipyridine Using the compound obtained in Reference Example 47 as a starting material, the title compound was obtained in the manner similar to that in Example 1. The product was recrystallized from ethyl acetate-hexane. A colorless prism crystal. M.p. 213 to 214° C.

EXAMPLE 11
Preparation of 3-chloro-4-(4-ethoxyphenyl)-5,6,7,8-tetrahydro-2-(succinimidomethyl)thieno[2,3-b:5,4-c'] dipyridine To a solution of the compound obtained in Reference Example 48 (3 g) in methylene chloride (100 ml) was added dropwise iodotrimethylsilane (2.5 ml) at room temperature, and then the mixture was stirred for 1 hour at room temperature. After addition of methanol (30 ml) and stirring for further 15 minutes, the solution was concentrated under reduced pressure. The residue thus obtained was subjected to column chromatography on silica gel. A fraction eluted with chloroform-methanol (20:1, v/v) was collected and concentrated under reduced pressure. The residue thus obtained was dissolved in ethyl acetate (50 ml), washed with saturated aqueous sodium bicarbonate, water and brine, dried ($MgSO_4$), and then the solvent was distilled off to obtain the title compound (673 mg, 29%). The product was recrystallized from ethyl acetate-methanol. A colorless prism crystal. M.p. 215 to 217° C.

EXAMPLE 12
Preparation of 3-chloro-5,6,7,8-tetrahydro-2-(succinimidomethyl)-4-[4-(2,2,2-trifluoroethoxyphenyl)] thieno[2,3-b:5,4-c']dipyridine Using the compound obtained in Reference Example 49 as a starting material, the title compound was obtained in the manner similar to that in Example 11. The product was recrystallized from ethyl acetate-hexane. A colorless prism crystal. M.p. 193 to 194° C.

EXAMPLE 13
Preparation of 3-chloro-4-(4-ethylphenyl)-5,6,7,8-tetrahydro-2-(succinimidomethyl)thieno[2,3-b:5,4-c'] dipyridine Using the compound obtained in Reference Example 50 as a starting material, the title compound was obtained in the manner similar to that in Example 11. The product was recrystallized from ethyl acetate. A colorless prism crystal. M.p. 157 to 158° C.

EXAMPLE 14
Preparation of 4-(4-benzyloxyphenyl)-3-chloro-5,6,7,8-tetrahydro-2-(succinimidomethyl)thieno[2,3-b:5,4-c'] dipyridine Using the compound obtained in Reference Example 51 as a starting material, the title compound was obtained in, the manner similar to that in Example 11. The product was, recrystallized from tetrahydrofuran-hexane. A colorless prism crystal. M.p. 247 to 248° C.

EXAMPLE 15
Preparation of 3-chloro-4-(4-hydroxyphenyl)-5,6,7,8-tetrahydro-2-(succinimidomethyl)thieno[2,3-b:5,4-c'] dipyridine To a solution of the compound obtained in Example 14 (600 mg) in methylene chloride (20 ml) was added titanium tetrachloride (1.1 g) while cooling with ice. After stirring for 2 hours at room temperature followed by addition of water (10 ml), the stirring was continued for further 15 minutes. After discontinuing the stirring, the aqueous layer was isolated, and neutralized with saturated aqueous sodium bicarbonate, and then extracted with ethyl acetate-tetrahydrofurane (3:1, v/v). The extracted organic layer was washed with water, dried ($MgSO_4$) and then the solvent was distilled off to obtain the title compound (305 mg, 62%). The product was recrystallized from dimethylformamide-water. A colorless prism crystal. M.p. 286 to 287° C.

EXAMPLE 16
Preparation of 7-acetyl-3-chloro-5,6,7,8-tetrahydro-4-(4-methoxyphenyl)-2-(succinimidomethyl)thieno[2,3-b:5,4-c'] dipyridine To a solution mixture containing the compound obtained in Example 1 (1 g), triethylamine (343 mg) and tetrahydrofuran (50 ml) was added acetic anhydride (254 mg) while cooling with ice. After stirring for 2 hours at room temperature, the reaction solution was concentrated under reduced pressure. The residue thus obtained was dissolved in ethyl acetate (50 ml), washed with water, dried (MgSO$_4$) and then the solvent was distilled off to obtain the title compound (582 mg, 53%). The product was recrystallized from tetrahydrofuran. A colorless prism crystal. M.p. 266 to 267° C.

EXAMPLE 17

Preparation of 7-acetyl-3-chloro-4-(4-ethoxyphenyl)-5,6,7,8-tetrahydro-2-(succinimidomethyl)thieno[2,3-b:5,4-c']dipyridine Using the compound obtained in Example 11 as a starting material, the title compound was obtained in the manner similar to that in Example 16. The product was recrystallized from tetrahydrofuran-methanol. A colorless prism crystal. M.p. 260 to 262° C.

EXAMPLE 18

Preparation of 7-acetyl-3-chloro-4-(3,4-dimethoxyphenyl)-5,6,7,8-tetrahydro-2-(succinimidomethyl)thieno[2,3-b:5,4-c']dipyridine Using the compound obtained in Example 2 as a starting material, the title compound was obtained in the manner similar to that in Example 16. The product was recrystallized from ethanol. A colorless prism crystal. M.p. 208 to 210° C.

EXAMPLE 19

Preparation of 7-acetyl-3-chloro-5,6,7,8-tetrahydro-4-(4-hydroxyphenyl)-2-(succinimidomethyl)thieno[2,3-b:5,4-c']dipyridine To a solution of the compound obtained in Example 15 (640 mg) in pyridine (30 ml) was added acetic anhydride (336 mg) while cooling with ice. After stirring for 14 hours at room temperature, the reaction solution was concentrated under reduced pressure. The residue was dissolved in ethyl acetate (25 ml), washed with water, dried (MgSO$_4$), and then the solvent was distilled off. The residue was subjected to column chromatography on silica gel. The fraction eluted with hexane-ethyl acetate (5:1, v/v) was collected and the solvent was distilled off. The residue thus obtained, which was combined with saturated aqueous sodium bicarbonate (15 ml), methanol (30 ml), water (15 ml) and tetrahydrofurane (30 ml), was stirred for 3 hours at room temperature, and then neutralized with 1N hydrochloric acid. The crystal precipitated was isolated by filtration, and washed with methanol to obtain the title compound (406 mg, 58%). The product was recrystallized from tetrahydrofuran-methanol. A colorless prism crystal. M.p. 300° C. or higher.

EXAMPLE 20

Preparation of 3-chloro-5,6,7,8-tetrahydro-4-(4-isopropoxy-3-methoxyphenyl)-2-(succinimidomethyl)thieno[2,3-b:5,4-c']dipyridine Using the compound obtained in Reference Example 52 as a starting material, the title compound was obtained in the manner similar to that in Example 1. The product was recrystallized from ethyl acetate-hexane. A colorless prism crystal. M.p. 175 to 176° C.

EXAMPLE 21

Preparation of 7-acetyl-3-chloro-5,6,7,8-tetrahydro-4-(4-isopropoxy-3-methoxyphenyl)-2-(succinimidomethyl)thieno[2,3-b:5,4-c']dipyridine Using the compound obtained in Example 20 as a starting material, the title compound was obtained in the manner similar to that in Example 16. The product was recrystallized from tetrahydrofuran-hexane. A colorless prism crystal. M.p. 242 to 243° C.

EXAMPLE 22

Preparation of 7-acetyl-3-chloro-5,6,7,8-tetrahydro-4-(4-hydroxy-3-methoxyphenyl)-2-(succinimidomethyl)thieno[2,3-b:5,4-c']dipyridine Using the compound obtained in Example 21 as a starting material, the title compound was obtained in the manner similar to that in Example 15. The product was recrystallized from tetrahydrofuran-hexane. A colorless prism crystal. M.p. 273 to 275° C.

The structures of the compounds obtained in the above Example 1 to 22 are shown in the following Table 7 and Table 8.

TABLE 7

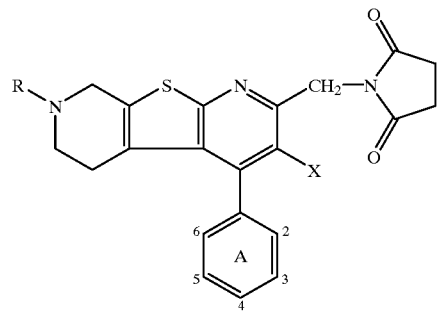

| Example No. | R | X | Substituent for the ring A | |
|---|---|---|---|---|
| 1 | H | Cl | 4-position: | —OCH$_3$ |
| 2 | H | Cl | 3-position: | —OCH$_3$ |
|   |   |   | 4-position: | —OCH$_3$ |
| 3 | H | Cl | 4-position: | —OCH$_2$CH$_2$CH(CH$_3$)$_2$ |
| 4 | H | Br | 4-position: | —OCH$_3$ |
| 5 | H | Cl | 4-position: | Cl |
| 6 | H | Cl | 4-position: | CF$_3$ |
| 7 | H | Cl | 4-position: | —C(CH$_3$)$_3$ |
| 8 | H | Cl | 4-position: | —CH(CH$_3$)$_2$ |
| 9 | H | Cl | 4-position: | —NH—CO—CH$_3$ |
| 10 | H | Cl | 4-position: | —COOC$_2$H$_5$ |
| 11 | H | Cl | 4-position: | —OC$_2$H$_5$ |

TABLE 8

| Example No. | R | X | Substituent for the ring A |
|---|---|---|---|
| 12 | H | Cl | 4-position: —OCH$_2$CF$_3$ |
| 13 | H | Cl | 4-position: —C$_2$H$_5$ |
| 14 | H | Cl | 4-position: —OCH$_2$—C$_6$H$_5$ |
| 15 | H | Cl | 4-position: —CH |
| 16 | CH$_3$CO— | Cl | 4-position: —OCH$_3$ |
| 17 | CH$_3$CO— | Cl | 4-position: —OC$_2$H$_5$ |
| 18 | CH$_3$CO— | Cl | 3-position: —OCH$_3$; 4-position: —OCH$_3$ |
| 19 | CH$_3$CO— | Cl | 4-position: —OH |
| 20 | H | Cl | 3-position: —OCH$_3$; 4-position: —OCH(CH$_3$)$_2$ |
| 21 | CH$_3$CO— | Cl | 3-position: —OCH$_3$; 4-position: —OCH(CH$_3$)$_2$ |
| 22 | CH$_3$CO— | Cl | 3-position: —OCH$_3$; 4-position: —OH |
| 27 | C$_2$H$_5$CO— | Cl | 4-position: —OCH$_3$ |
| 28 | CF$_3$CO— | Cl | 4-position: —OCH$_3$ |

EXAMPLE 23

10 mg of the compound obtained in Example 1, 90 mg of lactose, 70 mg of micro crystalline cellulose and 5 mg of magnesium stearate are mixed, and the mixture is granulated. 5 mg of magnesium stearate is added to the granulated, and they are mixed together. The mixture is encapsulated with gelatin capsules.

EXAMPLE 24

10 mg of the compound obtained in Example 2, 35 mg of lactose, 150 mg of corn starch, 20 mg of micro crystalline celluose and 2.5 mg of magnesium stearate are mixed, and the mixture is granulated. 10 mg of micro crystalline cellulose and 2.5 mg of magnesium stearate are added to the granules, and they are mixed together. The mixture is compression-molded to obtain tablets.

EXAMPLE 25

10 mg of the compound obtained in Example 18, 100 mg of inositol and 150 mg of benzyl alcohol are dissolved in distilled water for injection as totaled 2 ml, and the solution is filled into ampoules. All processes are done in aseptic conditions.

EXAMPLE 26

10 mg of the compound obtained in Example 22, 35 mg of lactose, 150 mg of corn starch, 20 mg of micro crystalline cellulose and 2.5 mg of magnesium stearate are mixed, and the mixture is granulated. 10 mg of micro crystalline cellulose and 2.5 mg of magnesium stearate are added to the granules, and they are mixed together. The mixture is compression-molded to obtain tablets.

EXAMPLE 27

Preparation of 3-chloro-5,6,7,8,-tetrahydro-4-(4-methoxyphenyl)-2-(succinimidomethyl)-7-propionylthieno[2,3-b: 5,4-c']dipyridine To a stirred mixture containing the compound obtained Example 1 (500 mg) in pyridine (10 ml) was added dropwise propionyl chloride (0.1 ml) with ice-cooling. After stirring at room temperature for 3 hr, the solvent was evaporated off. The residue was dissolved in ethyl acetate, washed successively with water and brine, dried (MgSO$_4$) and concentrated in vacuo to give the title compound (287 mg, 51%). The product was recrystallized from ethyl acetate. A colorless prism crystal. M.p. 236 to 237° C

EXAMPLE 28

Preparation of 3-chloro-5,6,7,8-tetrahydro-4-(4-methoxyphenyl)-2-(succinimidomethyl)-7-(trifluoroacetyl)thieno[2,3-b: 5,4-c']dipyridine Using the compound obtained in Example 1 and trifluoroacetic anhydride as starting materials, the title compound was prepared in the manner similar to that in Example 27. The product was recrystallized from ethyl acetate-methanol. A colorless prism crystal. M.p. 250 to 252° C.

The structures of the compounds obtained in the above Example 27 and 28 are shown in the above-mentioned Table 8.

TEST EXAMPLE 1

Action Against Rat Adjuvant Arthritis:

Male Lewis rats (7 weeks of age, Clea Japan) were sensitized by intracutaneous injection of 0.05 ml of Freund's complete adjuvant (0.5% dead *Mycobacterium Tuberculosis* suspension in liquid paraffin) at the right hind paw. The test drug (3.13 mg/kg), in suspension in 0.5% methyl cellulose, was once daily administered for 14 days starting just before sensitization (day 0). At day 14, the animal's left hind paw volume was measured using a plethysmometer (produced by Ugo Basile Company, Italy), and paw swelling suppression rate (%) were determined.

The results, expressed in mean ±S.E. for each group (N=6), were compared and statistically analyzed by Dunnett's test. Level of significance was set below 5%. The results were shown in Table 9.

TABLE 9

| Compound (Example No.) | Swelling suppression rate (%) |
|---|---|
| 1 | 94** |
| 2 | 92** |
| 4 | 85** |
| 11 | 98** |
| 18 | 92** |
| 22 | 75** |

**; $p < 0.05$ vs control

As shown in Table 9, the compound of the present invention was effective in relieving systemic symptoms, as assessed by paw edema suppression.

TEST EXAMPLE 2

Stability Against Metabolism by Liver Microsome:

A dog liver microsome was prepared by a standard method. In a phosphate buffer (pH 7.4), a test substance, a liver microsome and NADPH-producing system [0.5 mM, β-NADP (NADP: nicotinamide adenine dinucleotide phosphate), 1 mM magnesium chloride, 5 mM glucose-6-phosphate, 150units/ml glucose-6-phosphate dehydrogenase (each as final concentration in reaction system)] were mixed and incubated at 37° C. The concentration of the test substance after the discontinuation of the reaction was determined by high pressure liquid chromatography to obtain % residue (n=2, mean). The results are shown in Table 10.

TABLE 10

| Compound (Example No.) | Residue (%) |
|---|---|
| 1 | 90.5 |
| 2 | 87.8 |
| 11 | 94.1 |
| 15 | 96.3 |

As evident from Table 10, any of the compounds according to the present invention exhibited a higher stability against metabolism by a liver microsome.

INDUSTRIAL APPLICABILITY

Compound (I) according to the present invention or a salt thereof has an excellent anti-inflammatory effect and accordingly is useful as an anti-inflammatory agent, especially as a pharmaceutical for treating arthritis, and also has an excellent bone resorption suppressing effect and thus is useful for preventing or treating bone destruction or osteoporosis accompanying arthritis, and also has an excellent immune cytokine production suppressing effect and thus is useful for preventing or treating a disease involving the immune system including autoimmune disease, and also is useful for preventing or treating rejection after organ transplantation. In addition, compound (I) according to the present invention or a salt thereof has a stability against biological metabolism, which allows it to exert its efficacy for a prolonged period and to be used advantageously as a pharmaceutical.

What is claimed is:

1. A compound of the formula (I):

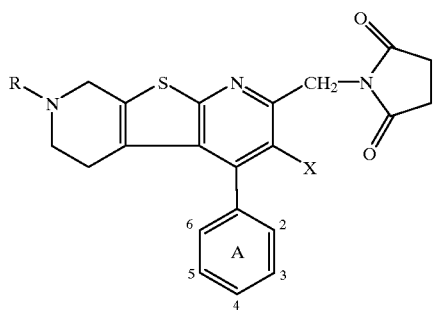

wherein R is hydrogen or $C_{2-6}$ alkanoyl; X is halogen; and ring A is benzene ring which is optionally substituted by 1 to 4 substituents selected from (1) halogen, (2) hydroxy, (3) $C_{1-6}$ alkoxy optionally substituted by halogen or phenyl, (4) $C_{1-6}$ alkylthio optionally substituted by halogen or phenyl, (5) $C_{1-6}$ alkyl optionally substituted by halogen, (6) $C_{2-6}$ alkanoylamino or (7) carboxy optionally esterified by $C_{1-6}$ alkyl, or a producing or a pharmaceutically acceptable salt thereof.

2. A compound of claim 1 wherein R is hydrogen.

3. A compound of claim 1 wherein ring A is benzene ring which is optionally substituted by 1 to 2 substituents selected from (1) hydroxy, (2) $C_{1-6}$ alkoxy optionally substituted by halogen or (3) $C_{1-6}$ alkylthio optionally substituted by halogen.

4. A compound of claim 1 wherein R is hydrogen; and ring A is benzene ring which is optionally substituted by 1 to 2 substituents selected from (1) $C_{1-6}$ alkoxy optionally substituted by halogen or (2) $C_{1-6}$ alkylthio optionally substituted by halogen.

5. A compound of claim 1 wherein R is hydrogen; X is chlorine; and ring A is benzene ring which is optionally substituted by 1 to 2 $C_{1-6}$ alkoxy groups.

6. A compound of claim 5 wherein ring A is benzene ring substituted by $C_{1-6}$ alkoxy group at the 4-position and optionally substituted by $C_{1-6}$ alkoxy group at the other position.

7. A compound of claim 1 wherein R is hydrogen; X is chlorine; and ring A is benzene ring which is optionally substituted by 1 to 2 methoxy groups.

8. A compound of claim 1 wherein R is $C_{2-6}$ alkanoyl; and ring A is benzene ring which is optionally substituted by 1 to 2 substituents selected from (1) hydroxy, (2) $C_{1-6}$ alkoxy optionally substituted by halogen or (3) $C_{1-6}$ alkylthio optionally substituted by halogen.

9. A compound of claim 1, which is a pro-drug.

10. 3-chloro-5,6,7,8-tetrahydro-4-(4-methoxyphenyl)-2-(succinimidomethyl)thieno{2,3-b:5,4-c'}dipyridine, 3-chloro-(3,4dimethoxyphenyl)-5,6,7,8-tetrahydro-2-(succinimidomethyl)thieno{2,3-b:5,4-c'}dipyridine, or a pharmaceutically acceptable salt thereof.

11. 3-chloro-4-(4-ethoxyphenyl)-5,6,7,8-tetrahydro-2-(succinimidomethyl)thieno{2,3-b:5,4-c'}dipyridine, 3-bromo-5,6,7,8-tetrahydro-4-(4-methoxyphenyl)-2-(succinimidomethyl)thieno{2,3-b:5,4-c'}dipyridine, or a pharmaceutically acceptable salt thereof.

12. 7-acetyl-3-chloro-5,6,7,8-tetrahydro-4-(4-hydroxy-3-methoxyphenyl)-2-(succinimidomethyl)thieno{2,3-b:5,4-c'}dipyridine, 7-acetyl-3-chloro-5,6,7,8-tetrahydro-4-(4-hydroxyphenyl)-2-(succinimidomethyl)thieno{2,3-b:5,4-c'}dipyridine, or a pharmaceutically acceptable salt thereof.

13. 7-acetyl-3-chloro-5,6,7,8-tetrahydro-4-(4-methoxyphenyl)-2-(succinimidomethyl)thieno{2,3-b:5,4-c'}dipyridine, 7-acetyl-3-chloro-4-(4-ethoxyphenyl)-5,6,7,8-tetrahydro-2-(succinimidomethyl)thieno{2,3-b:5,4-c'}dipyridine, 7-acetyl-3-chloro-4-(3,4-dimethoxyphenyl)-5,6,7,8-tetrahydro-2-(succinimidomethyl)thieno{2,3-b:5,4-c'}dipyridine, or a pharmaceutically acceptable salt thereof.

14. A method for production of a compound of the formula (I-2):

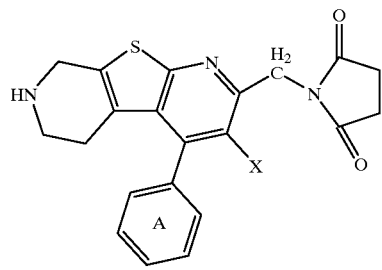

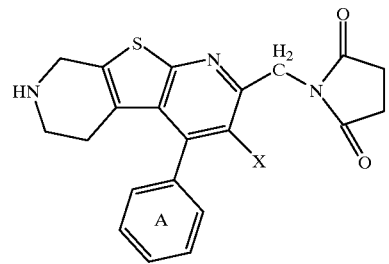

wherein X is halogen atom; ring A is benzene ring which is optionally substituted by 1 to 4 substituents selected from (1) halogen, (2) hydroxy, (3) $C_{1-6}$ alkoxy optionally substituted by halogen phenyl, (4) $C_{1-6}$ alkylthio optionally substituted by halogen phenyl, (5) $C_{1-6}$ alkyl optionally substituted by halogen, (6) $C_{2-6}$ alkanoylamino (7) carboxyl optionally esterified by $C_{1-6}$ alkyl, or a pharmaceutically acceptable salt thereof, which comprises subjecting a compound of the formula:

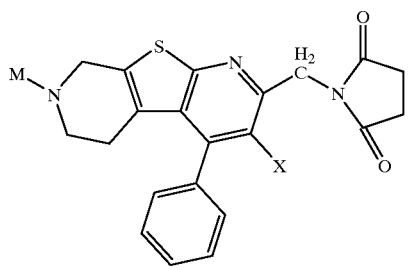

where M is a protective group of a nitrogen atom and wherein X is halogen atom; ring A is benzene ring which is optionally substituted by 1 to 4 substituents selected from (1) halogen, (2) hydroxy, (3) $C_{1-6}$ alkoxy optionally substituted by halogen phenyl, (4) $C_{1-6}$ alkylthio optionally substituted by halogen phenyl, (5) $C_{1-6}$ alkyl optionally substituted by halogen, (6) $C_{2-6}$ alkanoylamino or (7) carboxyl optionally esterified by $C_{1-6}$ alkl, a salt thereof, to deprotection.

15. A method for production of a compound of the formula (I-3):

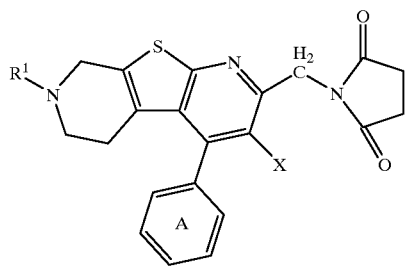

wherein $R_1$ is $C_{2-6}$ alkanoyl; X is halogen; ring A is benzene ring which is optionally substituted by 1 to 4 substituents selected from (1) halogen, (2) hydroxy, (3) $C_{1-6}$ alkoxy optionally substituted by halogen phenyl, (4) $C_{1-6}$ alkylthio optionally substituted by halogen phenyl, (5) $C_{1-6}$ alkyl optionally substituted by halogen, (6) $C_{2-6}$ alkanoylamino or (7) carboxyl optionally esterified by $C_{1-6}$ alkyl, or a pharmaceutically acceptable salt thereof, which comprises subjecting a compound of the formula (I-2):

wherein X is halogen; ring A is benzene ring which is optional substituted by 1 to 4 substituents selected from (1) halogen, (2) hydroxy, (3) $C_{1-6}$ alkoxy otionally substituted by halogen or phenyl, (4) $C_{1-6}$ alkylthio optionally substituted by halogen phenyl, (5) $C_{1-6}$ alkyl optionally substituted by halogen, (6) $C_{2-6}$ akanoylamino or (7) carboxyl optionally esterified by $C_{1-6}$ alkyl, or a salt thereof, to acylation.

16. A pharmaceutical composition comprising a compound of the formula (I):

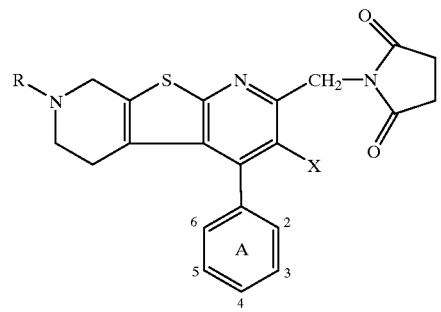

wherein R is hydrogen or $C_{2-6}$ alkanoyl; X is halogen; and ring A is benzene ring which is optionally substituted by 1 to 4 substituents selected from (1) halogen, (2) hydroxy, (3) $C_{1-6}$ alkoxy optionally substituted by halogen or phenyl, (4) $C_{1-6}$ alkylthio optionally substituted by halogen or phenyl, (5) $C_{1-6}$ alkyl optionally substituted by halogen (6) $C_{2-6}$ alkanoylamino or (7) carboxyl optionally esterified by $C_{1-6}$ alkyl, or a pharmaceutically acceptable salt thereof.

17. A pharmaceutical composition of claim 16 which is for treating inflammatory disease.

18. A pharmaceutical composition of claim 16 which is for treating arthritis.

19. A pharmaceutical composition of claim 16 which is for treating rheumatism.

20. A pharmaceutical composition of claim 16 which is for treating chronic rheumatoid arthritis.

21. A pharmaceutical composition of claim 16 which is for treating autoimmune disease.

22. A pharmaceutical composition of claim 16 which is for treating rejection after organ transplantation.

23. A method for treating inflammatory disease in a mammal which comprises administering an effective amount of the pharmaceutical composition of claim 16 to said mammal in need thereof.

24. A method for treating arthritis in a mammal which comprises administering an effective amount of the pharmaceutical composition of claim 16 to said mammal in need thereof.

25. A method for treating rheumatism in a mammal which comprises administering an effective amount of the pharmaceutical composition of claim 16 to said mammal in need thereof.

26. A method for treating chronic rheumatoid arthritis in a mammal which comprises administering an effective amount of the pharmaceutical composition of claim 16 to said mammal in need thereof.

27. A method for treating autoimmune disease in a mammal which comprises administering an effective amount of the pharmaceutical composition of claim 16 to said mammal in need thereof.

28. A method for treating rejection after organ transplantation in a mammal which comprises be administering an effective amount of the pharmaceutical composition of claim 16 to said mammal in need thereof.

29. A method for making a pharmaceutical composition for treating rejection after organ transplantation comprising mixing the compound of claim 1 with a pharmaceutically acceptable carrier.

30. A method for making a pharmaceutical composition for treating arthritis comprising mixing the compound of claim 1 with a pharmaceutically acceptable carrier.

31. A method for making a pharmaceutical composition for treating chronic rheumatoid arthritis comprising mixing the compound of claim 1 with a pharmaceutically acceptable carrier.

32. A method for making a pharmaceutical composition for treating an autoimmune disease comprising mixing the compound of claim 1 with a pharmaceutically acceptable carrier.

33. A method for making a pharmaceutical composition for treating arthritis comprising mixing the compound of claim 1 with a pharmaceutically acceptable carrier.

\* \* \* \* \*